United States Patent [19]
Vande Woude et al.

[11] Patent Number: 6,150,398
[45] Date of Patent: *Nov. 21, 2000

[54] METHODS FOR THE TREATMENT OF CANCER

[75] Inventors: George F. Vande Woude, Berryville, Va.; Nicholas Schulz, Pittsburgh, Pa.; Renping Zhou; Ira Daar, both of Frederick, Md.; Marianne Oskarsson, Gaitherburg, Md.

[73] Assignee: The United States of America as represented by the Department of Health and Human Services, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/618,863

[22] Filed: Mar. 20, 1996

Related U.S. Application Data

[62] Division of application No. 08/169,962, Dec. 20, 1993, abandoned, which is a continuation of application No. 07/880,525, May 8, 1992, abandoned, which is a continuation-in-part of application No. 07/696,923, May 8, 1991, abandoned.

[51] Int. Cl.[7] .................................................. C07D 305/14
[52] U.S. Cl. .......................... 514/449; 549/510; 549/511; 424/649
[58] Field of Search ........................... 514/449; 549/510; 424/649

[56] References Cited

U.S. PATENT DOCUMENTS

| | | |
|---|---|---|
| 4,357,352 | 11/1982 | Swallow . |
| 4,535,058 | 8/1985 | Weinberg et al. . |
| 4,569,916 | 2/1986 | Penman et al. . |
| 4,701,406 | 10/1987 | Chou . |
| 4,798,787 | 1/1989 | McCormick et al. . |
| 4,814,470 | 3/1989 | Colin et al. .............................. 514/449 |
| 4,820,631 | 4/1989 | Lacal et al. . |
| 4,871,838 | 10/1989 | Bos et al. . |
| 4,885,238 | 12/1989 | Reddel et al. . |
| 4,942,184 | 7/1990 | Huagwitz . |
| 4,960,790 | 10/1990 | Stella et al. .............................. 514/449 |
| 4,996,145 | 2/1991 | Weisenthal . |
| 5,034,544 | 7/1991 | Elliott . |
| 5,114,951 | 5/1992 | King . |
| 5,124,330 | 6/1992 | King . |
| 5,124,338 | 6/1992 | King . |
| 5,124,339 | 6/1992 | King . |
| 5,160,727 | 11/1992 | Klohs et al. . |
| 5,208,238 | 5/1993 | King . |
| 5,262,409 | 11/1993 | Margolis et al. . |
| 5,300,282 | 4/1994 | King . |
| 5,346,897 | 9/1994 | King . |
| 5,364,843 | 11/1994 | King . |
| 5,387,685 | 2/1995 | Powell et al. . |
| 5,395,610 | 3/1995 | King . |
| 5,447,936 | 9/1995 | Hausheer et al. . |
| 5,449,663 | 9/1995 | Bicher . |
| 5,468,754 | 11/1995 | Hausheet et al. . |

OTHER PUBLICATIONS

Boven, et al., *Cancer Research*, 45, 86–90 (1985).
Du Bois et al., *Seminars in Oncology*, 24 (5), S15–44–S15–52 (1997).
Eisenberger, et al. *J. Clin. Oncol.*, 7 (9), 1341–1345 (1989).
Gadduci et al., *Anticancer Research*, 17, 4703–4708 (1997).
Hannan et al., *Toxicology*, 55, 183–191 (1989).
Holmes et al., *J. Natl. Cancer Inst.*, 83 (24), 1979–1805 (1991).
Kavanagh, *Cancer Bulletin (Houston)*, 42 (2), 89–93 (1990).
Kelsen et al., *Seminars in Oncology*, 24 (6), S19–77–S19–81 (1997).
Maugh, *Science*, 194, 310 (1976).
McGuire et al., *Annals of Internal Medicine*, 111 (4), 273–279 (1989).
Micetich et al., *Cancer Research*, 45, 4043–4047 (1985).
Nio, et al. *J. Surg. Oncol.*, 48, 252–259 (1991).
Ringel et al., *J. Natl. Cancer Inst.*, 83 (4), 288–291 (1991).
Rowinsky et al., *Proc. Am. Soc. Clin. Oncol.*, 7, 136 (1988).
Salmon, et al., *J. Clin. Oncol.*, 12 (11), 2405–2414 (1994).
Sorensen, *Seminars in Oncology*, 24 (4), S12–18–S12–20 (1997).
Allende et al., *FEBS Lett.*, 234, 426–430 (1988).
Barbacid, *Ann. Rev. Biochem.*, 56, 779–827 (1987).
Barber, *Yale Journal of Biology and Medicine*, 64, 127–141 (1991).
Barrett et al., *Mol. Cell Biol.*, 10, 310–315 (1990).
Birchmeier et al., *Cell*, 43, 615–621 (1985).
Bravo, *Cell Growth & Differentiation*, 1, 305–309 (1990).
Brewer et al., *Cancer Treatment Reports*, 71, 353–359 (1987).
Cadman et al., *Science*, 205, 1135–1137 (1979).
Caldas et al., *J. of the National Cancer Institute Monographs*, 15, 155–159 (1993).
Caldas et al., *Seminars in Oncology*, 20, 50–55 (1993).
Chabner et al., *Cancer Chemotherapy and Biological Response Modifiers Annual*, 11, 74–81 (Elsevier Science Publishers B.V., 1990).
Chackalaparampil et al., *Cell*, 52, 801–810 (1988).
Citardi et al., *Proc. AACR*, 31, 410 (1990).
Coughlin et al., *Science*, 243, 1191–1194 (1989).
Daar et al, *Mol. Cell Biol.*, 11, 5985–5991 (1991).
Daar et al., *J. Cell. Biol.*, 114, 329–335 (1990).
Daar et al., *Science*, 253, 74–76 (1991).

(List continued on next page.)

*Primary Examiner*—Julie Burke
*Attorney, Agent, or Firm*—Leydig, Voit & Mayer, Ltd.

[57] ABSTRACT

A pharmaceutical composition comprising an effective cancerous cell growth inhibiting amount of paclitaxel, or a paclitaxel derivative, and an effective cancerous cell growth inhibiting amount of an active agent which inhibits cancerous cell growth by exerting an effect on mammalian cell cycle during $G_1$ or S-phase of the cell division cycle to inhibit said cancerous cell growth and methods of using same.

40 Claims, 20 Drawing Sheets

OTHER PUBLICATIONS

Delaporte et al., *Exp. Cell Res.*, 197, 176–182 (1991).
Deshpande et al., *Mol. Cell Biol.*, 7, 1285–1288 (1987).
Ducommun et al., *Analytical Biochemistry*, 187, 94–97 (1990).
Dumont, *J. Morphol.*, 136, 153–180 (1972).
Dunphy et al., *Cell*, 54, 423–431 (1988).
Durkin et al., *Mol. Cell Biol.*, 7, 444–449 (1987).
Feig et al., *Mol. Cell Biol.*, 8, 3235–3243 (1988).
Fischinger et al., *J. Gen. Virol.*, 13, 203–214 (1971).
Frankel et al., *J. Virol.*, 21, 153–160 (1977).
Freeman et al., *Proc. Natl. Acad. Sci. USA*, 86, 5805–5809 (1989).
Gautier et al., *Cell*, 54, 433–439 (1988).
Gautier et al., *Cell*, 60, 487–494 (1990).
Gerhart et al., *J. Cell Biol.*, 98, 1247–1255 (1984).
Gupta et al., *British J. Cancer*, 58, 441–447 (1988).
Hagag et al., *Oncogene*, 5, 1481–1489 (1990).
Hartwell et al., *Science*, 246, 629–634 (1989).
Heidemann et al., *J. Cell. Sci.*, 77, 129–141 (1985).
Heidemann et al., *Dev. Biol.*, 80, 489–494 (1980).
Hellman et al., *Cancer: Principles and Practice of Oncology*, 1st Ed., Philadelphia, JB Lippencott, 73–79, 132–155 (1982).
Hirakawa et al., *Proc. Natl. Acad. Sci. USA*, 85, 1519–1523 (1988).
Jones et al., *Proc. Natl. Acad. Sci. USA*, 77, 2651–2655 (1980).
Kaplan et al., *Cell*, 61, 125–133 (1990).
Kazlauskas et al., *Science*, 247, 1578–1581 (1990).
Kim et al., *Mol. Cell Biol.*, 10, 5945–5949 (1990).
Kishimoto et al., *Exp. Cell Res.*, 137, 121–126 (1982).
Kishimoto et al., *J. Exp. Zool.*, 231, 293–295 (1984).
Korn et al., *Science*, 236, 840–843 (1987).
Korn et al., *J. of Clinical Oncology*, 11, 794–801 (1993).
Kypta et al., *Cell*, 62, 481–492 (1990).
Kumjian et al., *Proc. Natl. Acad. Sci. USA*, 86, 8232–8236 (1989).
Lacal et al., *EMBO J.*, 5, 679–687 (1986).
Lee et al., *Trends in Genetics*, 4, 287–290 (1988).
Lohka et al., *J. Cell. Biol.*, 98, 1222–1230 (1984).
Lohka et al., *J. Cell. Biol.*, 101, 518–523 (1985).
Lohka et al., *Proc. Natl. Acad. Sci. USA*, 85, 3009–3013 (1988).
Margolis et al., *Cell*, 57, 1101–1107 (1989).
Markman et al., *Gynecologic Oncology*, 45, 3–8 (1992).
Masui et al., *J. Exp. Zool.*, 177, 129–146 (1971).
Masui et al., *Int. Rev. Cytol.*, 57, 185–282 (1979).
McGuire, *J. of the National Cancer Institute*, 81, 1438–1439 (1989).
McGuire, *Hematology/Oncology Clinics of North America*, 6, 927–940 (1992).
McGuire, *Gynecologic Oncology*, 51, 78–85 (1993).
McGuire, *Cancer Supplement*, 71, 1541–1550 (1993).
McGuire III et al., *J. of Clinical Oncology*, 7, 1462–1468 (1989).
Meyerhoff et al., *Dev. Biol.*, 61, 214–229 (1977).
Miake–Ley et al., *Cell*, 41, 165–175 (1985).
Morrison et al., *Cell*, 58, 649–657 (1989).
Murray et al., *Nature*, 339, 275–280 (1989).
Murray et al., *Science*, 246, 614–621 (1989).
Murray et al., *Nature*, 339, 280–286 (1989).
Newport et al., *Cell*, 30, 675–686 (1984).
Newport et al., *Cell*, 37, 731–742 (1984).
O'Keefe et al., *Proc. Natl. Acad. Sci. USA*, 86, 7038–7042 (1989).
Oskarsson et al., *Science*, 207, 1222–1224 (1980).
Papkoff et al., *Cell*, 29, 417–426 (1982).
Pardee et al., *Science*, 246, 603–608 (1989).
Park et al., *The Metabolic Basics of Inherited Disease*, 1, Chapter 5, 251–276 (Scriver et al., eds.) (McGraw–Hill New York, 1989).
Paules et al., *Proc. Natl. Acad. Sci. USA*, 86, 5395–5399 (1989).
Propst et al., *Nature*, 315, 516–518 (1985).
Ridley et al., *EMBO J.*, 7, 1635–1645 (1988).
Rollins et al., *Adv. Cancer Res.*, 53, 1–32 (1989).
Rowinsky et al., *Proc. ASCO*, 9, (1990).
Rowinsky et al., *J. Clin. Oncol*, "Sixth International Symposium on Platinum and Other Metal Coordinatio Compounds in Cancer Chemotherapy", University of California, San Diego Cancer Center (1991).
Rowinsky et al., *J. of Clinical Oncology*, 9, 1692–1703 (1991).
Rowinsky et al., *J. of Clinical Oncology*, 9, 1704–1712 (1991).
Roy et al., *Cell*, 61, 825–831 (1990).
Rubinstein et al., *J. Nat'l Cancer Inst.*, 82, 1113–1118 (1990).
Sagata et al., *Nature*, 335, 519–525 (1988).
Sagata et al., *Science*, 245, 643–646 (1989).
Sagata et al., *Nature*, 342, 512–518 (1989).
Schiff et al., *Nature*, 277, 665–667 (1979).
Schiff et al., *Proc. Natl. Acad. Sci. USA*, 77, 1561–1565 (1980).
Skehan et al., *J. Nat'l Cancer Inst.*, 82, 1107–112 (1990).
Smith et al., *Dev. Biol.*, 25, 232–247 (1971).
Tachibana et al., *J. Cell Sci.*, 88, 273–282 (1987).
Trimble et al., *Gynecologic Oncology*, 55, S114–S121 (1994).
Vale, *Cell*, 64, 827–839 (1991).
Vande Woude et al., *1990 Views of Cancer Research, General Motors Research Foundation*, 128–143 (1990).
Vogt et al., *Adv. Cancer Res.*, 55, 1–35 (1990).
Watanabe et al., *Nature*, 342, 505–511 (1989).
Willumsen et al., *EMBO J.*, 3, 2581 (1984).
Wilson et al., *Carcinogenesis*, 10, (4), 635–640 (1989).
Zhou et al., *Science*, 251, 671–675 (1991).
Jekunen et al., "Synergistic interaction between cisplatin and taxol in human ovarian carcinoma cells in vitro," *Br.J.Cancer*, 69, 299–306 (1994).
Yeh et al., "Synergistic Action of Taxol with Tiazofurin and Methotrexate in Human Breast Cancer Cells: Schedule–Dependence," *Life Sciences*, 54 (24), PL431–PL435 (1994).
Budavari et al The Merck Index 11th edition p. 1435, 1989.
Markman et al Yake Journal of Biology and medicine vol. 64 583–590, 1991.
Jekunen et al British Journal of Cancer vol. 69 299–306, 1994.
Rose et al Anti–Cancer Drugs vol. 3 311–321, 1992.
Niloff Current Opinion in Obstetrics and Gynecology vol. 3 66–72, 1991.
McGuire et al Annals of Internal Medicine vol. 111 273–279, 1989.
Thigpen et al proceedings of ASCO vol 9 Abstarct 604 p. 156, Mar. 1990.
Eriksson et al Seminars in Oncology Nursing vol. 6 No. 3 214–227, Aug. 1990.

"Phase I Study of Taxol (NSC 125973) and Cisplatin in Patients with Advanced Solid Tumors," Principal Investigator: Eric K. Rowinski, M.D.

"A Phase III Radomized Study of Cyclophosphamide (NSC#26271) and Cisplatin (NSC #119875) Versus Taxol (NSC#125973) and Cisplatin (NSC #119875) In Patients with Suboptimal Stage III and Stage IV Epithelial Ovarian Carcinaoma," William P. McGuire M.D. and William J. Hoskins M.D., Study Chairmen, Taxol Protocols CA 129–022, Section 8/10, vol. 1, pp. 206–460.

Rowinsky et al., "Pharmacologic, Pre–Clinical and Clinical Investigations of the Cisplatin/Taxol Combination," in *Platinum and Other Metal Coordination Compounds in Cancer Chemotherapy* (S.B. Howell, ed.), pp. 441–452 (1991).

The Pink Sheet, 54(24), T&G–8–T&G–9 (Jun. 11, 1990).

Yoshizaki et al., *Int. J. Gynecol. Cancer,* 5 (Suppl. 1), 51, Abstract 180 (1995).

Rose, *Monogr. Natl. Cancer Inst.,* 15, 47–53 (1993).

Rowinsky et al., *J. Cancer Res. Clin. Oncol.,* 119, 727–733 (1993).

Rowinsky et al., *J. Clin. Oncol.,* 11, 2010–2020 (1993).

Saunders et al., *Proc. AACR,* 33, 442 (1992).

Speicher et al., *Proc. AACR,* 33, 439 (1992).

Taxol = 0 μM

100:1

1,000:1

10,000:1

Taxol = 1 μM

100:1

1,000:1

10,000:1

METHODS FOR THE TREATMENT OF CANCER

This is a divisional of applications Ser. No. 08/169,962, filed on Dec. 20, 1993, now abandoned which, in turn, is a continuation of application Ser. No. 07/880,525, filed on May 8, 1992, now abandoned, which, in turn, is a continuation-in-part of application Ser. No. 07/696,923, filed on May 8, 1991, now abandoned.

TECHNICAL FIELD OF THE INVENTION

The present invention concerns a method for designing cancer treatments and evaluating the efficacy of anticancer drugs. The present invention also concerns methods and pharmaceutical compositions for the treatment of cancer.

BACKGROUND OF THE INVENTION

Duplication of genetic information and its partitioning to progeny cells are fundamental to all eukaryotes. Many lines of evidence suggest that oncogenes and tumor suppressor genes belong to the hierarchy of genes that regulate these processes. Oncogenes are normally positive regulators of the cell cycle and when activated, represent a gain of function in the cell. In contrast, tumor suppressor genes are negative regulators and promote transformation through their loss of function. While the number of oncogenes discovered continues to increase, the number of families to which they have been assigned has not. This may be due to the limited number of assays available for their detection, but it may also indicate that most of the families have been identified. The assignment of oncogenes to families was originally based upon their function, structural and sequence homology, or product localization, but the families appear to be taking on a new significance in the relationship with participation in the cell cycle.

Recent studies of signal transduction pathways in somatic cells have linked the products of one oncogene family either directly or indirectly to the activation of members of other families. For example, the stimulation of certain growth factor receptors by their appropriate growth factor or ligand results in the association of receptors directly with the src and raf products (Morrison et al., Cell, 58, 649–657 (1989); Kypta et al., Cell, 62, 481–492 (1990)). The receptors also associate with several proteins involved in second message pathways (e.g., PLC$\gamma$, PI3 kinase) (Coughlin et al., Science, 243, 1191–1194 (1989); Kumjian et al., Proc. Natl. Acad. Sci. USA, 86, 8232–8236 (1989); and Margolis et al., Cell, 57, 1101–1107 (1989)) as well as with a GTPase activating protein (GAP) that enhances the activity of the ras gene product. (Kaplan et al., Cell, 61, 125–133 (1990); Kazlauskas et al., Science, 247, 1578–1581 (1990)). Mitogenic stimulation of certain tyrosine kinase growth factor receptors results in specific transcriptional induction of a well-characterized series of genes, several of which are nuclear oncogenes. (Rollins et al., Adv. Cancer Res., 53, 1–32 (1989); Vogt et al., Adv. Cancer Res., 55, 1–35 (1990); Bravo R., Cell Growth & Differentiation, 1, 305–309 (1990)).

In contrast, however, understanding how such diverse gene families elicit expression of the transformed phenotype has not been so obvious. The fact that the members of these families function in the same or parallel pathways begins to address the problem of assigning hierarchy and determining whether a particular family is "upstream" or "downstream" in the pathway. It is obvious that growth factors or, for that matter, nuclear transcription regulators cannot be proximal effectors of the transformed phenotype. Assuming that most of the oncogene families have been identified, the most likely candidates for proximal effectors would be members of the kinase oncogene family, since they might modify nuclear and/or cytoskeletal proteins necessary for induction of morphological alterations associated with the neoplastic phenotype. Knowledge of such hierarchy is important for it may provide a means to develop strategies to intervene in neoplastic transformation.

Another major question is how these genes influence cell cycle. Restriction points in the cell cycle regulate entry into S-phase and M-phase and these control points are present in all species from yeast through man. The gene products that mediate and control these restriction points are being characterized. The cell cycle has been intensively studied in the budding yeast Saccharomyces cerevisiae and the fission yeast Schizosaccharomyces pombe. These yeasts are as distant from each other in evolution as they are from mammals. In spite of this, certain cell cycle regulators are conserved not only in structure, but also in function. Thus, CDC28/cdc2 genes from budding and fission yeasts are functionally equivalent. The product of this gene is a serine kinase whose targets are influenced during the cell cycle by the appearance of proteins termed cyclins. Cyclins, so named because of their cyclic appearance during M-phase of the cell cycle, were first discovered in clams and sea urchins. Independently, an activity termed maturation promoting factor (MPF) was discovered in unfertilized amphibian eggs (Masui et al., J. Exp. Zool., 177, 129–146 (1971); Smith et al., Dev. Biol., 25, 233–247 (1971)) as the activity responsible for inducing meiotic maturation (Masui et al., Int. Rev. Cytol., 57, 185–292 (1979)). MPF was subsequently found in all M-phase cells undergoing meiosis or mitosis from yeast to man and is therefore considered the universal regulator of M-phase in eukaryotes (Kishimoto et al., Exp. Cell Res., 137, 121–126 (1982); Kishimoto et al., J. Exp. Zool., 231, 293–295 (1984); Tachibana et al., J. Cell Sci., 88, 273–282 (1987)). MPF is responsible for nuclear envelope breakdown and chromosome condensation (Lohka et al., J. Cell Biol., 98, 1222–1230 (1984); Lohka et al., J. Cell Biol., 101, 518–523 (1985); Miake-Lye et al., Cell, 41, 165–175 (1985)). Lohka et al. (Proc. Natl. Acad. Sci. USA, 85, 3009–3013 (1988)) first purified MPF, which was subsequently shown to consist of the amphibian homologs of the yeast p34$^{cdc2}$ gene product and cyclins (Gautier et al., Cell, 54, 433–439 (1988); Gautier et al., Cell, 60, 487–494 (1990)). Thus, in just a few years, an extraordinary series of discoveries allowed characterization of the major cell cycle regulator in species as diverse as yeast and man. The relationship between p34$^{cdc2}$ kinase and oncogenes or tumor suppressor genes is emerging.

There remains a need for techniques to identify suitable anticancer drugs and treatments and for new and efficacious methods and pharmaceutical compositions for the treatment of cancer in mammals, particularly humans. It is an object of the present invention to provide such techniques for identifying suitable anticancer drugs and treatments. It is another object of the present invention to provide methods and pharmaceutical compositions for the treatment of cancer.

These and other objects and advantages of the present invention, as well as additional inventive features, will be apparent from the description of the invention provided herein.

BRIEF SUMMARY OF THE INVENTION

The present invention is directed to a new approach for designing combinations of drugs for the treatment of cancer based on the discovery that it is desirable to use a drug which exerts its primary effect on mammalian cell cycle prior to or during S-phase in combination with a drug that exerts its primary effect on mammalian cell cycle after S-phase but prior to or during M-phase.

For example, a number of drugs can be screened for their ability to interfere with the mammalian cell cycle prior to or during S-phase and drugs can also be screened for their ability to interfere with the mammalian cell cycle after S-phase but prior to or during M-phase. An S-phase drug can then be used together with an M-phase drug for further screening to see if a synergistic anti-cancer effect is observed. If such an anti-cancer effect is observed, additional screening and testing on this combination can be conducted to determine whether or not the combination of drugs is therapeutically useful in a patient.

For combinations which are determined to be effective, the two drugs (the "S-phase" drug and the "M-phase" drug) can be administered to a patient (or a laboratory mammal such as a mouse, rabbit, hamster, guinea pig, etc.) at the same time as part of the same pharmaceutical composition or the two drugs can be administered to the patient in close proximity in time to each other so that a suitable level of both drugs is present in the patient whereby a synergistic effect can be achieved. Usually, the two drugs will be administered to the patient within 24 hours of each other, preferably within 8 hours of each other and more preferably within 1 hour of each other. The exact timing of administration may be affected by the half-life of the drugs, the toxicity of the drugs, etc. Known drugs will preferably be administered by the routes of administration and dosages currently approved by the FDA. However, when a synergistic effect is observed between two drugs, it is possible that each drug can be administered in a dosage which is lower than the dosage used when the drug is administered alone. Preferred methods for combination therapy administration of drugs are intravenous injection, bolus injection, continuous infusion, or delivery from an osmotic pump of the S-phase drug in close proximity in time to the administration of the M-phase drug by any of the above routes to treat patients (humans or mammals) suffering from malignancies. The doses of the S-phase drug and the M-phase drug used and the route of administration and the carriers and/or adjuvants used may vary based on the tumor type being treated and in view of known procedures for treatment of such tumors.

The present invention also relates to a method for designing an anticancer treatment regimen, which comprises selecting a first drug which acts at one checkpoint in the mammalian cell cycle; selecting a second drug which acts at a different checkpoint in the mammalian cell cycle; and testing said first and second drugs to determine if a complimentary anticancer effect is observed when the two drugs are used together. This method is based on the principle that certain anticancer drugs, and in particular combinations of anticancer drugs, are effective because they take advantage of a cancer cell's inability to repair itself and/or a cancer cell's inability to check the cell cycle to ensure the proper order of cell cycle events. The known check points in the cell cycle are summarized in Hartwell et al., *Science*, 246, 629–634 (1989). It may be desirable to use drugs which act at different checkpoints in combination therapy to treat cancer in an effort to achieve a complimentary anticancer effect which could not be achieved if the drugs were used alone or if two drugs which affect the same checkpoint are used together.

The present invention is also directed to a pharmaceutical composition for treating cancer which comprises an effective cancer cell growth inhibiting amount of paclitaxel or a paclitaxel derivative and an effective cancer cell growth inhibiting amount of another drug which exerts its primary effect at a different point of the mammalian cell cycle, preferably prior to or during S-phase. The paclitaxel derivatives useful in accordance with the present invention are preferably water-soluble taxol derivatives. Examples of suitable paclitaxel derivatives are described in U.S. Pat. No. 4,942,184 to Haugwitz which issued on Jul. 17, 1990. Suitable treatment regimens for such a pharmaceutical composition include a variety of administrative routes as described above, for example, infusion over suitable time periods at suitable doses, e.g., 170–300 mg/m$^2$/cycle.

The present invention is also directed to a method for testing whether a drug has activity at the $G_2/M_1$ border which comprises contacting a dividing fertilized embryo with a drug and measuring or observing cleavage arrest in the embryo. The drug is preferably applied to the embryo by injecting the drug into one cell of a Xenopus blastomere which contains two cells and comparing the rate of cleavage of the injected cell with the rate of cleavage of the other cell of the blastomere. However, the drug can be contacted with two separate cells in two separate test tubes and the rate of arrest of cleavage of the cell containing the drug under study can be compared with the rate of cleavage of the cell (control cell) which has not been contacted with the drug. If the drug causes an arrest in cleavage of the blastomere, then it is possible that this drug has activity at the $G_2/M_1$ border. An extract from the cleavage arrest cell can then be tested for MPF or histone H1 kinase by the MPF assay reported by Sagata et al., *Nature*, 355, 519–525 (1988) or the histone H1 kinase assay reported by Ducommun et al., *Analytical Biochemistry*, 187, 94–97 (1990). If the results are positive for either the MPF or histone H1 kinase assay, then this is a confirmation that the cleavage arrest was because the drug exerts its primary effect at the $G_2/M_1$ border.

The present invention is also directed to a method for evaluating the efficacy of anticancer drugs by contacting a mixture of a non-transformed parental cell line and an oncogene transformed derivative of the parental cell line with an anticancer drug or combination of anticancer drugs. A second mixture of the non-transformed parental cell line and derivative transformed by a different oncogene is contacted with the same anticancer drug or combination of drugs. The effect of the anticancer drug or drugs on the the oncogene transformed cell lines is compared to the non-transformed cell line and the effect of the anticancer drug or drugs on each oncogene transformed cell line is compared. A second anticancer drug or combination of drugs may be contacted with the same mixtures described above for comparison of different anticancer drugs on the same oncogene transformed cell lines. This method may also be used for predicting which human cancers are sensitive to an anticancer drug.

*laevis* (Sagata et al., *Nature*, 342, 512–518 (1989)). C-mos RNA is represented by dots and Mos protein by the hatched area. The developmental stages for oogenesis and embryogenesis are indicated. F, fertilization; FE, fertilized egg; G, gastrulation; GVBD, germinal vesicle breakdown; H, hatching; LB, lampbrush stage; MBT, mid-blastula transition; UFE, unfertilized egg; V, start of vitellogenesis; PG, progesterone (Watanabe et al., *Nature*, 342, 505–511 (1989)).

Figure 3A:
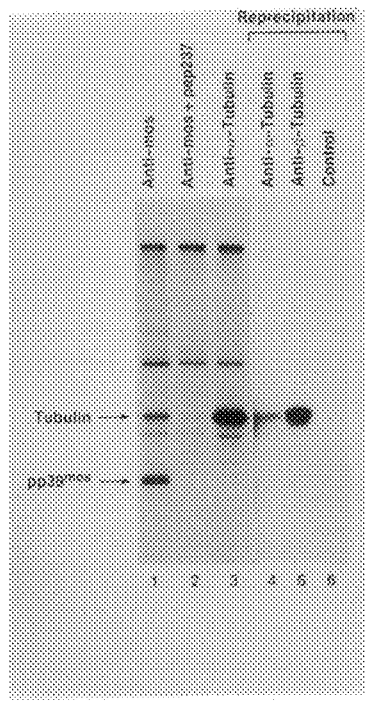

FIGS. 3A, B and C. Tubulin is coprecipitated with and phosphorylated by pp39$^{mos}$ (Zhou et al., *Science*, 251, 671–675 (1991)). (A) $^{35}$S-labeled tubulin was coprecipitated with pp39$^{mos}$ from c-mos$^{xe}$-transformed cells immunoprecipitated with 5S Mos monoclonal antibody. NIH/3T3 cells transformed by c-mos$^{xe}$ were labeled for 17 hours with [$^{35}$S]cysteine at a concentration of 0.5 mCi/ml in cysteine-free medium. The cytosol extract was immunoprecipitated with 5S Mos antibody in the absence of SDS without (lane 1) or with (lane 2) competing peptide. One-fourth of each sample was directly analyzed by SDS-PAGE (lanes 1 and 2). The remaining sample was boiled in 0.5% SDS as described and reprecipitated with either anti-α-tubulin (lane 4), anti-β-tubulin (lane 5), or a nonspecific monoclonal antibody (lane 6). α-Tubulin was also directly precipitated with the cytosol extract with anti-α-tubulin antibody (lane 3) and comigrated with the protein coprecipitated by pp39$^{mos}$ (lanes 1 and 4). (B) Both α- and β-tubulin were phosphorylated by pp39$^{mos}$ kinase in the immune complex isolated from c-mos$^{xe}$-transformed cells. Cytosol extracts from unlabeled c-mos$^{xe}$-transformed NIH/3T3 cells were prepared and immunoprecipitated with 5S Mos antibody as above. The in vitro kinase assay was performed with the immune complex. As in panel A, a portion of the reaction was analyzed directly by SDS-PAGE (lanes 1 and 2). The remaining samples were analyzed by reprecipitation with 5S Mos antibody (lane 3), α-tubulin antibody (lane 4), β-tubulin antibody (lane 5), or a nonspecific antibody (lane 6) as above. (C) α-Tubulin (lanes 2 and 4) and β-tubulin (lanes 2 and 5) from Xenopus oocytes also coprecipitated with and were phosphorylated by pp39$^{mos}$. The in vitro kinase assay and reprecipitation were performed with the immune complex of pp39$^{mos}$ from mature Xenopus oocytes as described in panel B.

Figure 4:
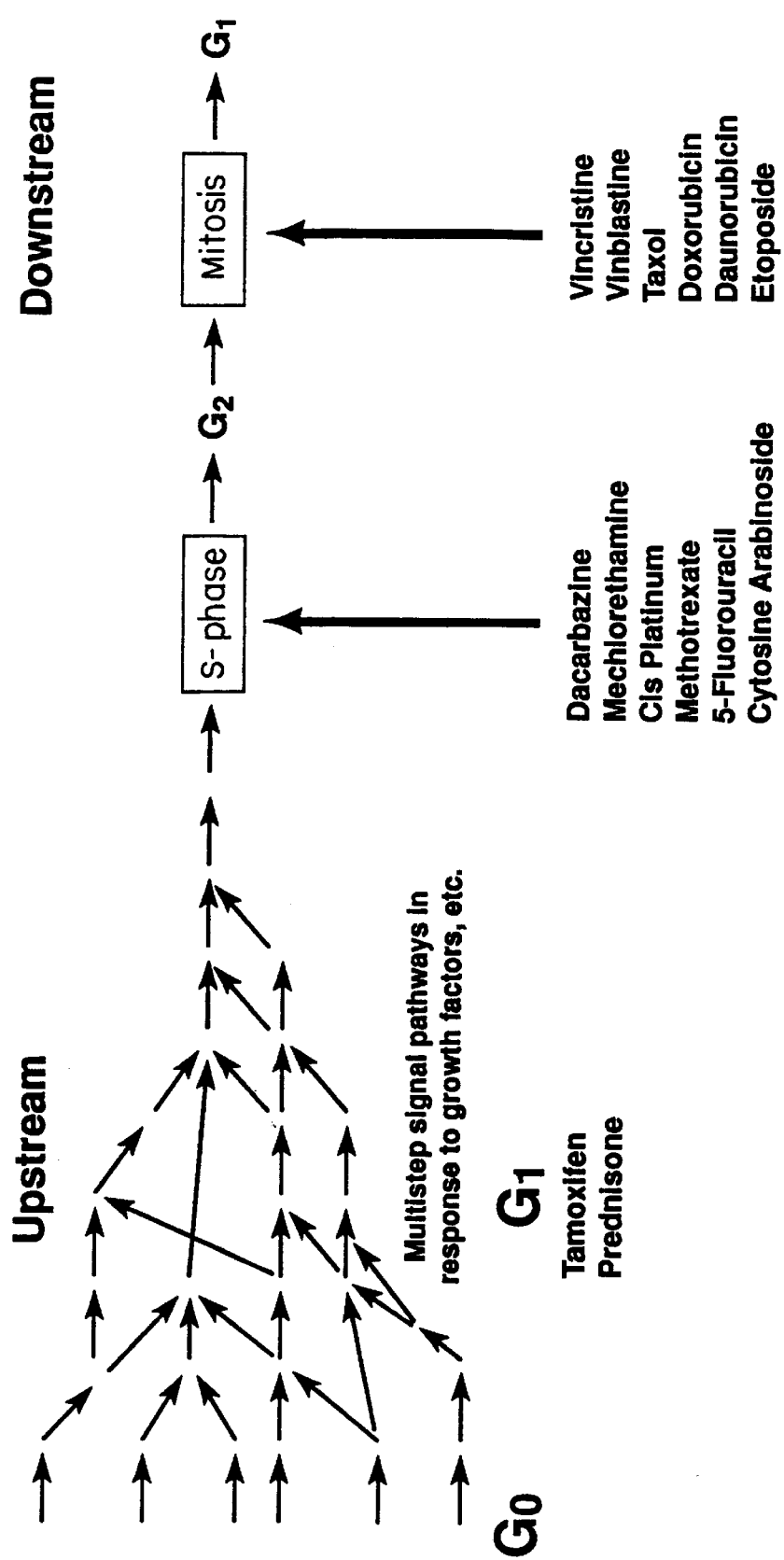

FIG. 4. Cell cycle regulation and points of drug interaction. This scheme represents a network of signal transduction pathways originating from different growth factors. These processes converge at the late G$_1$ control points. Cells continue through the cycle leading to S-phase and mitosis. The proposed points of drug interaction with the cell cycle are indicated (Lee et al., *Trends Genet.*, 4A 287–290 (1988)).

Figure 5:
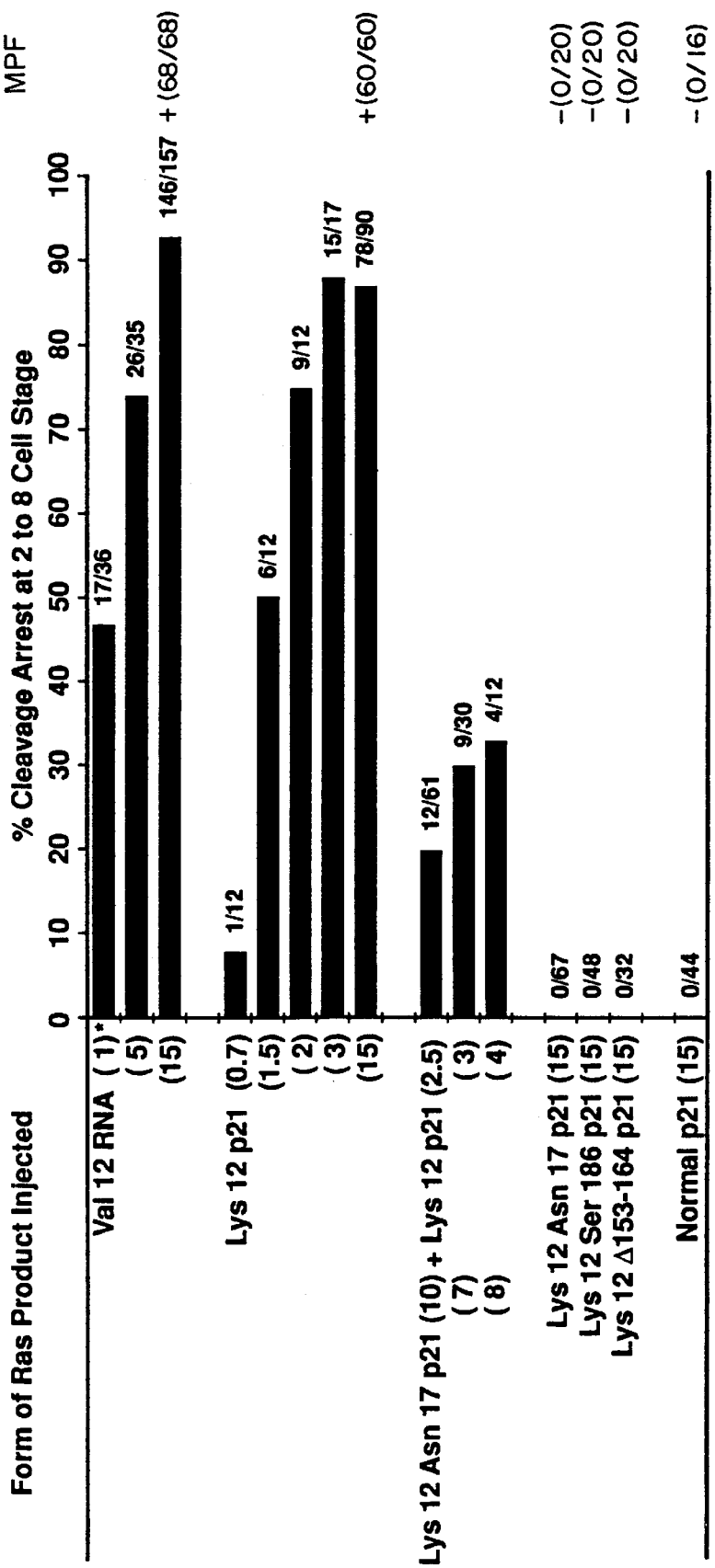

FIG. 5. Induction of cleavage arrest by injected RNA and protein. Ovulated eggs were obtained and fertilized in vitro (Kishimoto et al., *J. EXP. Zool.*, 231, 293–295 (1984)). The fertilized eggs were dejellied in 0.3× MMR containing 2% cysteine (pH 7.9) (Coughlin et al., *Science*, 243, 1191–1194 (1989)), then washed and placed in 0.3× MMR for 1.5 hours at 21° C. The 2-cell embryos were microinjected with a 30-nl solution containing the appropriate RNA or protein and incubated several hours longer in 0.3× MMR containing 5% Ficoll 400. The few injected blastomeres that ceased cleavage with irregular pigment patterns were omitted from the tabulated data. The fractions at the end of each histogram bar represent the number of embryos arrested in cleavage over the number of embryos injected. Crude MPF extracts were prepared (Lohka et al., *J. Cell Biol.*, 101, 518–523 (1985)) from groups of ten embryos 5 to 6 hours after they had been injected with the indicated solutions as described in Table 1. These extracts were tested for MPF activity (Lohka et al., *J. Cell Biol.*, 101, 518–523 (1985)).

Figure 6A:
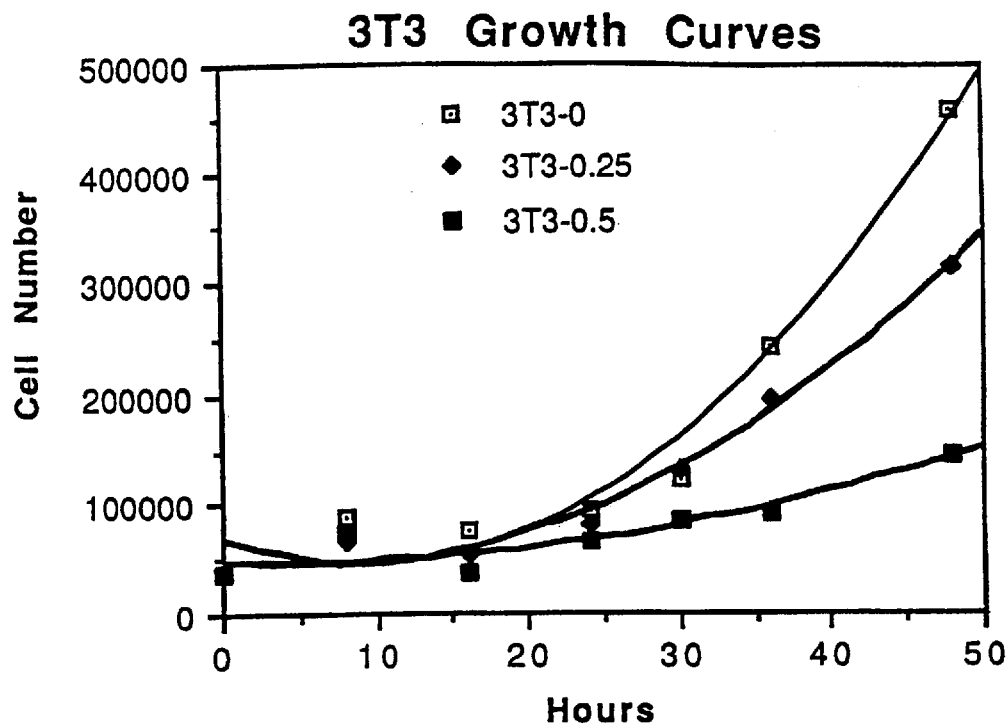
Figure 6B:
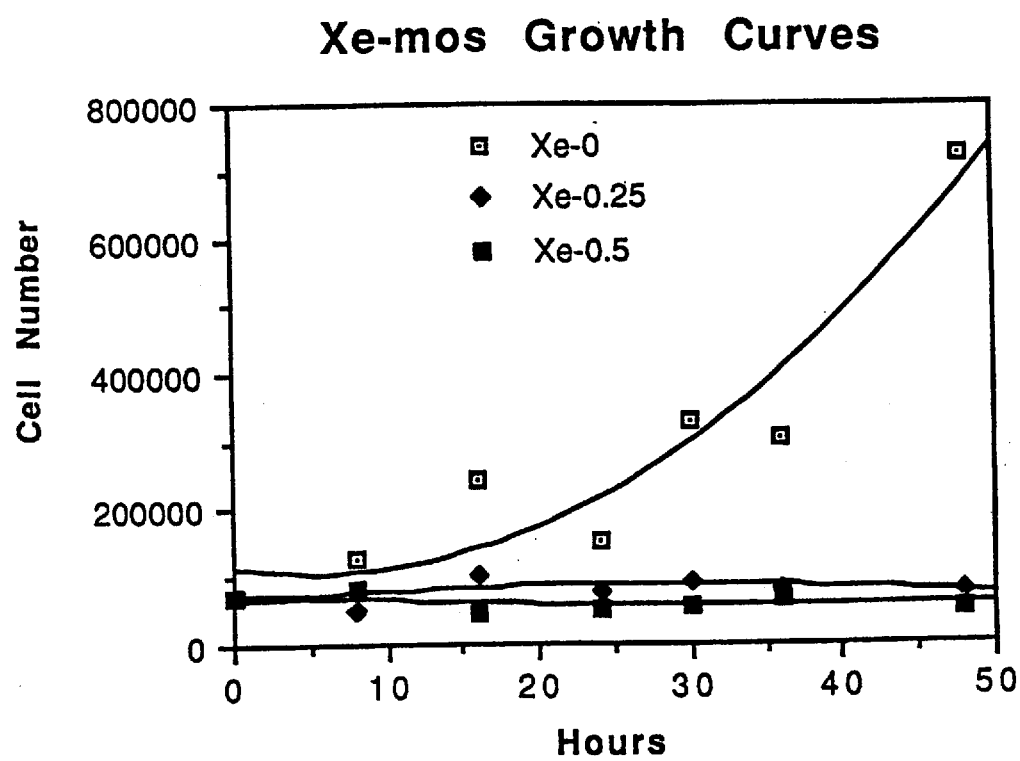
Figure 6C:
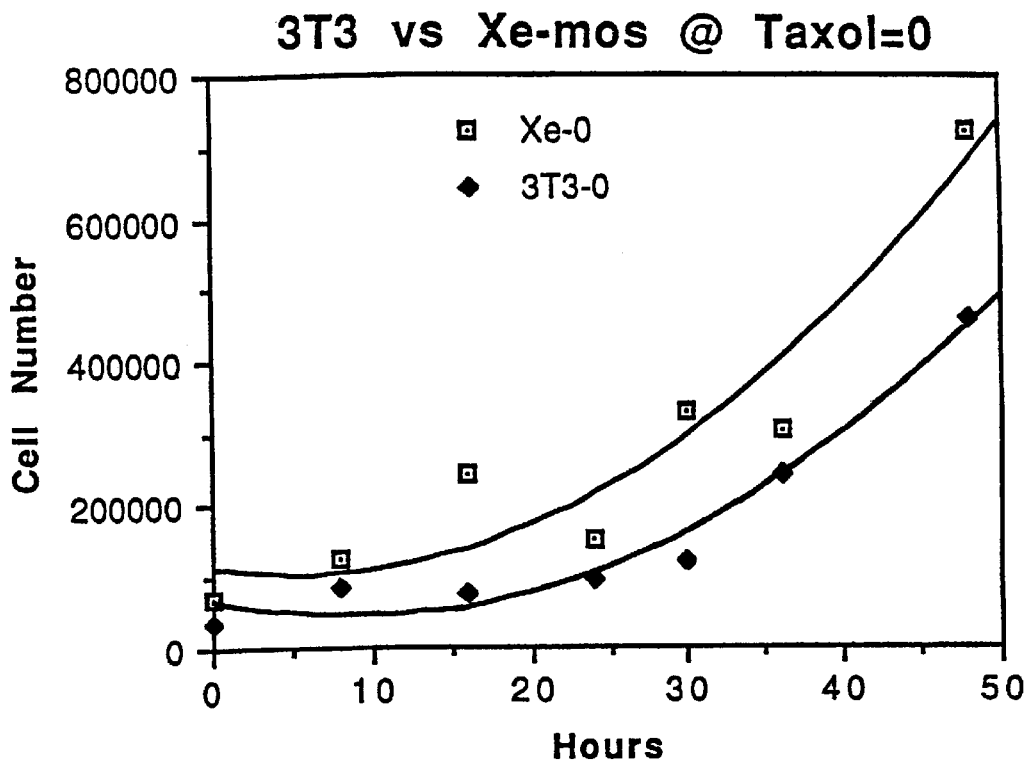
Figure 6D:
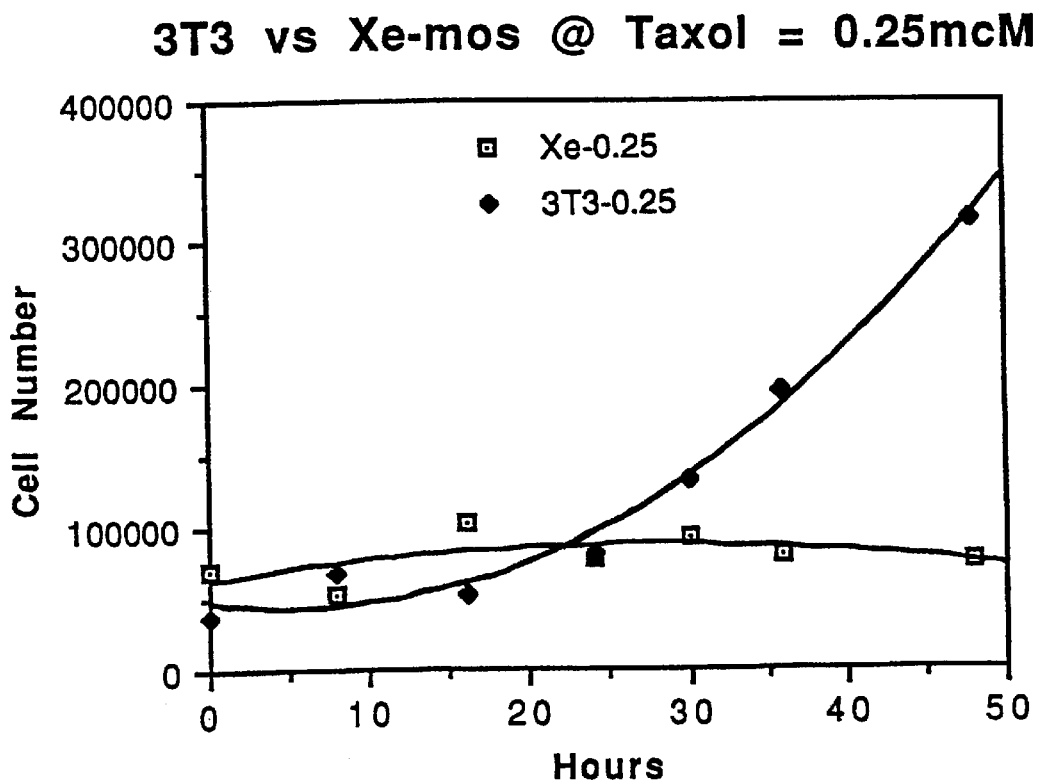

FIGS. 6A, B, C, D and E. FIG. 6A and FIG. 6B: Growth curve of 3T3 fibroblasts (FIG. 6A) and Xe-mos transformed fibroblasts (FIG. 6B) at 3 different paclitaxel concentrations: paclitaxel=0 μM (open squares); paclitaxel=0.25 μM (diamonds); paclitaxel=0.5 μM (solid squares). FIGS. 6C, D and E: Comparison of growth curves of transformed and non-transformed fibroblasts at 3 different paclitaxel concentrations (0, 0.25, and 0.5 μM taxol). Squares—mos-transformed; diamonds—non-transformed 3T3 fibroblasts.

Figure 7A:
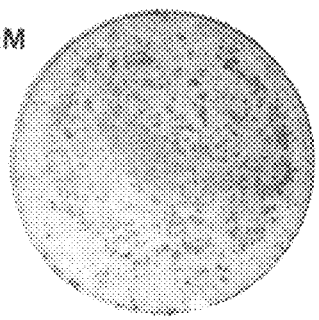
Figure 7B:
Figure 7C:
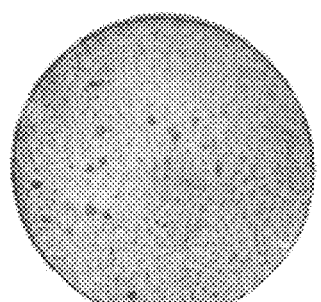
Figure 7D:
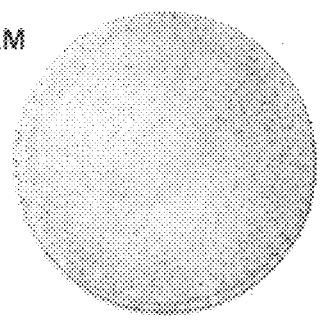
Figure 7E:
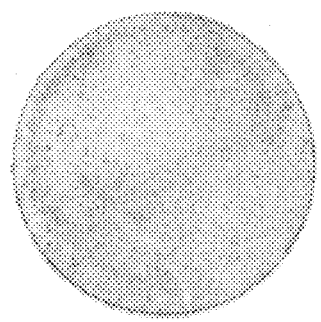
Figure 7F:
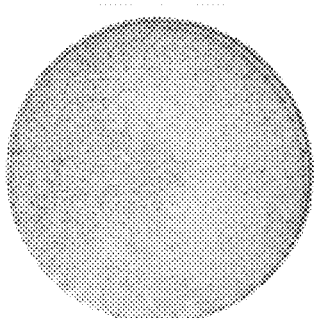
Figure 6E:
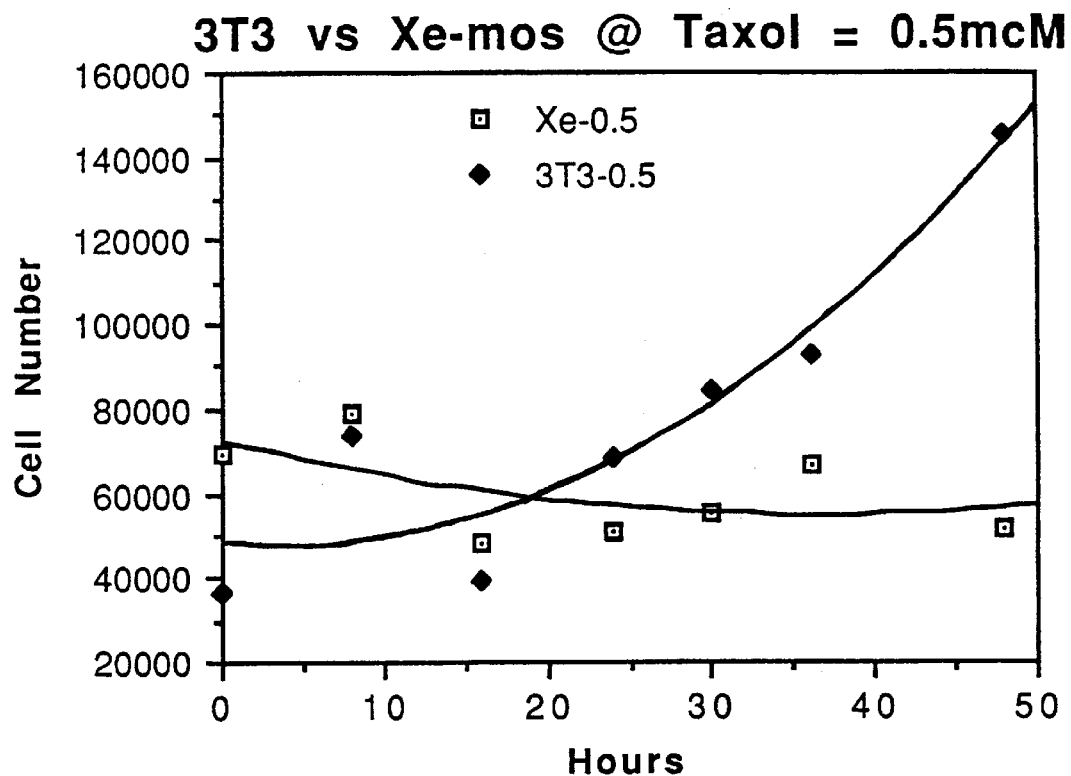

FIGS. 7A, B, C, D, E and F. contains photographs of the results of the cell culture experiments reported in Example 4.

Figure 8:
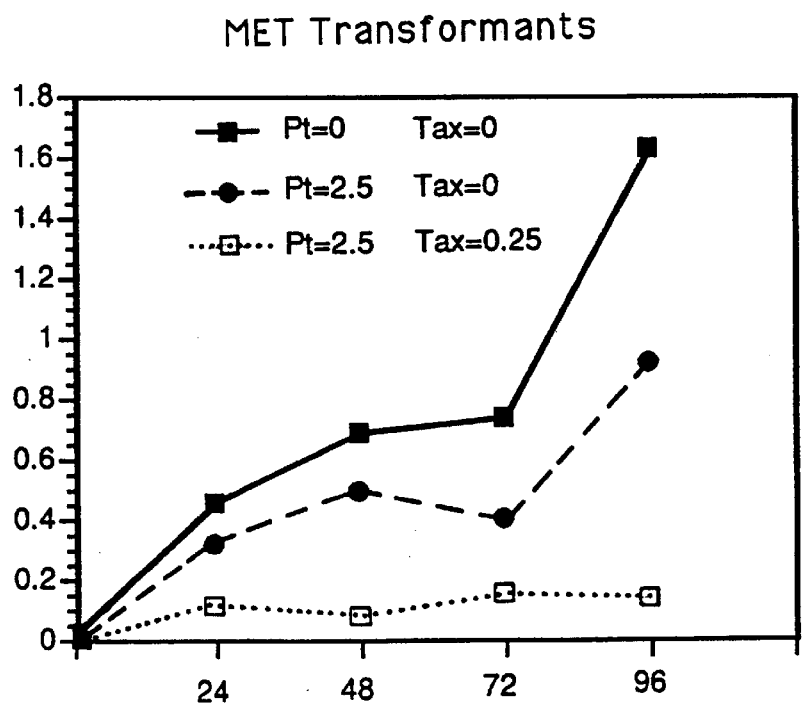

FIG. 8. Growth curve of Mu-met transformants at three different paclitaxel and cis-platinum concentrations: paclitaxel=0 μM, cis-platinum=0 μM (solid squares); paclitaxel=0 μM, cis-platinum=2.5 μM (circles); paclitaxel=0.25 μM, cis-platinum=2.5 μM (open squares).

Figure 9:
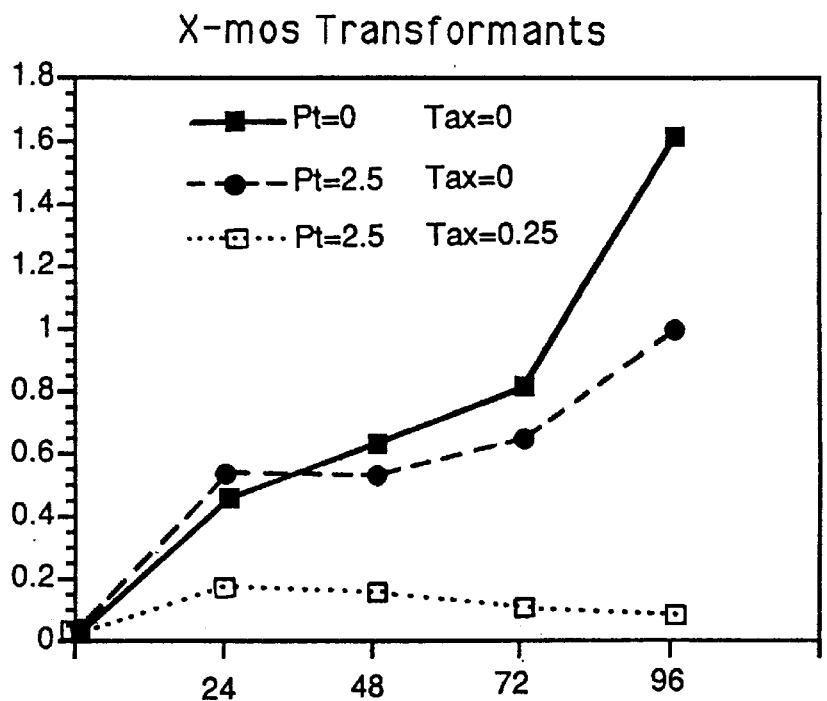

FIG. 9. Growth curve of X-mos transformants at three different paclitaxel and cis-platinum concentrations: paclitaxel=0 μM, cis-platinum=0 μM (solid squares); paclitaxel=0 μM, cis-platinum=2.5 μM (circles); paclitaxel=0.25 μM, cis-platinum=2.5 μM (open squares).

Figure 10A:
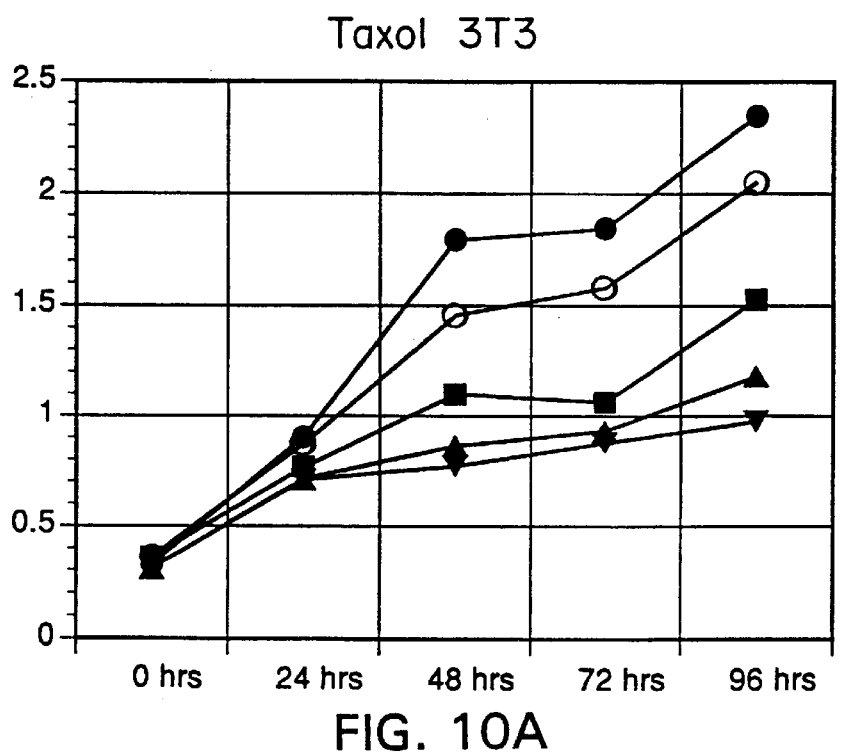
Figure 10B:
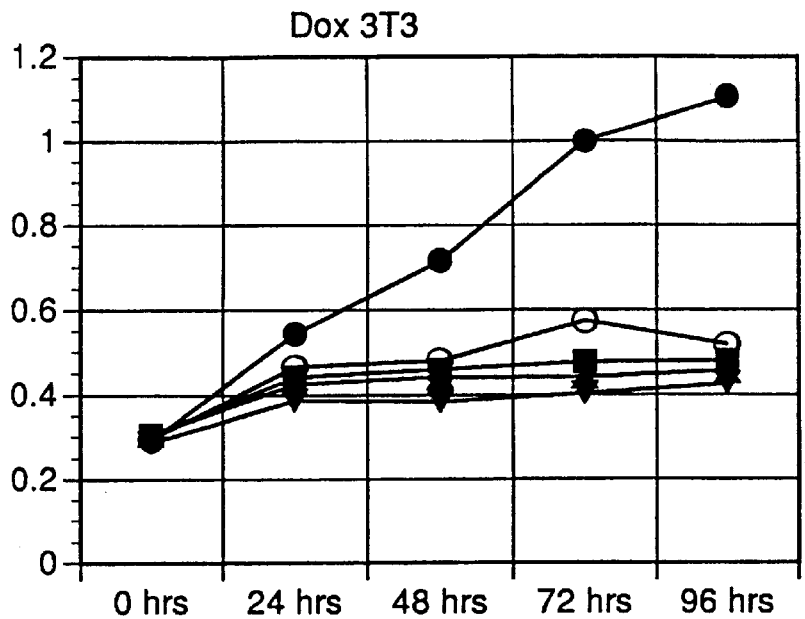
Figure 10C:
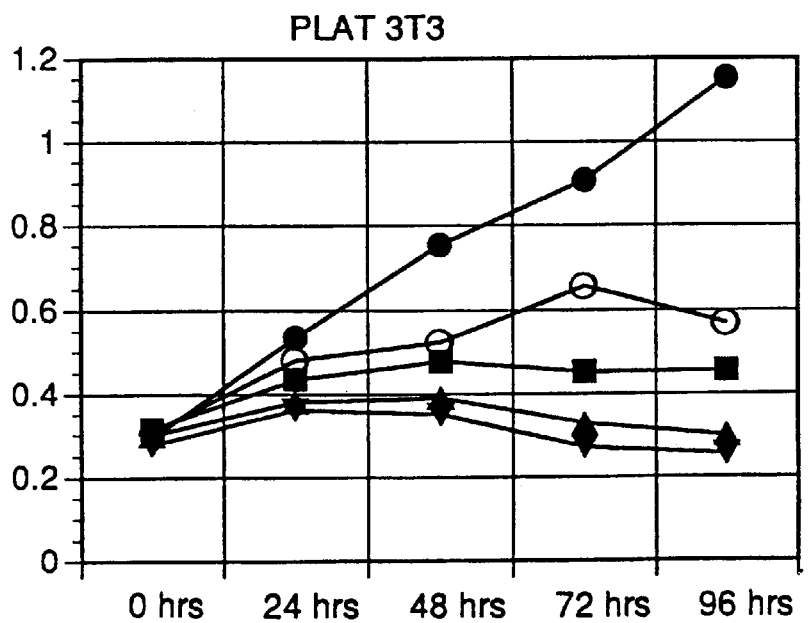
Figure 10D:
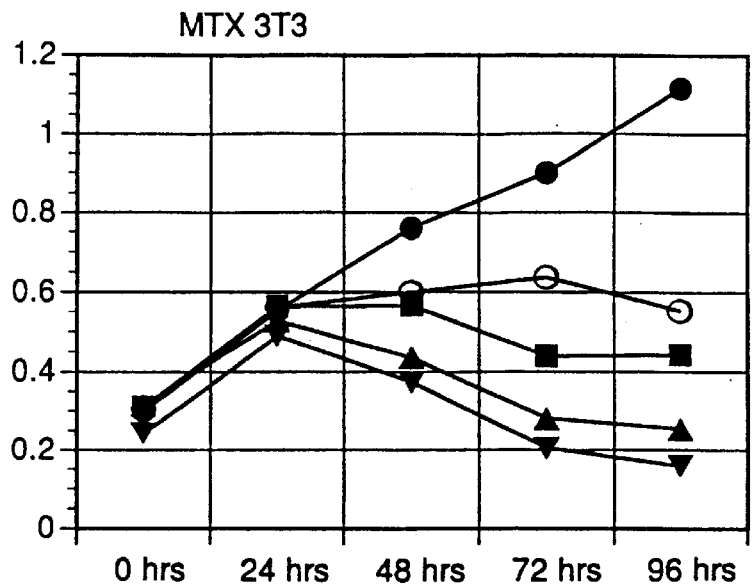

FIGS. 10A, B, C and D. FIGS. 10A and 10B: Growth curve of 3T3 fibroblasts at five different paclitaxel concentrations (FIG. 10A): paclitaxel=0 μM (solid circles); paclitaxel=0.5 μM (open circles); paclitaxel=1.0 μM (solid squares); paclitaxel=2.0 μM (right side up triangles); paclitaxel=5.0 μM (upside down triangles); and at three different doxorubicin concentrations (FIG. 10B): doxorubicin=0 μM (solid circle); doxorubicin 0.025 μM (open circle); doxorubicin=0.05 μM (solid squares); doxorubicin=0.1 μM (right side up triangles); doxorubicin=0.25 μM (upside down triangles). FIGS. 10C and 10D: Growth curves of 3T3 fibroblasts at five different cis-platinum concentrations (FIG. 10C): cis-platinum=0 μM (solid circles); cis-platinum=2.5 μM (open circles); cis-platinum=5.0 μM (solid squares); cis-platinum=10 μM (right side up triangles); cis-platinum=25 μM (upside down triangles); and a five different methotrexate concentrations (FIG. 10D): methotrexate=0 μM (solid circles); methotrexate=0.025 μM (open circles); methotrexate=0.05 μM (solid squares); methotrexate=0.1 μM (right side up triangles; methotrexate=0.25 μM (upside down triangles).

Figure 11A:
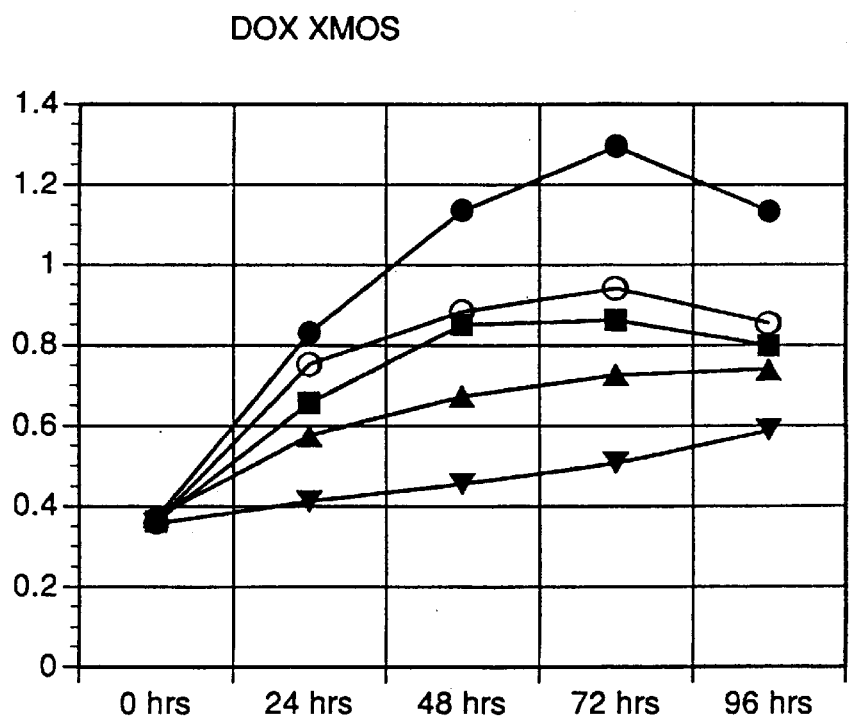
Figure 11B:
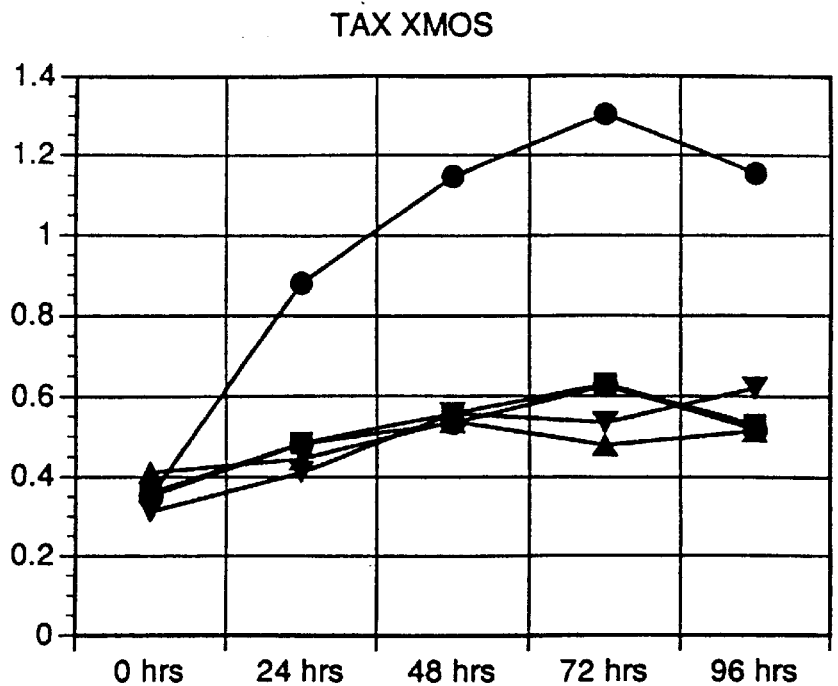
Figure 11C:
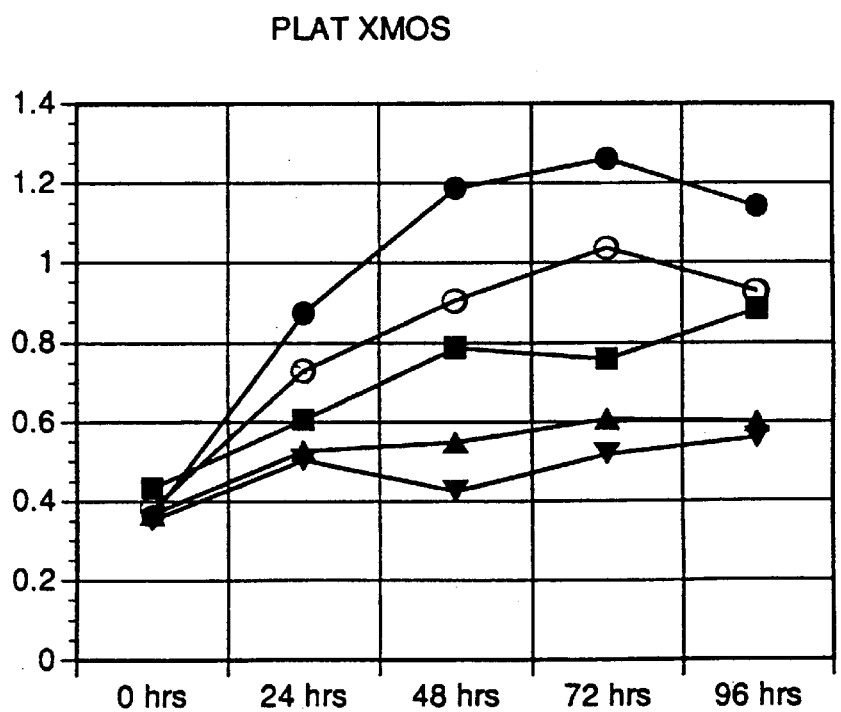
Figure 11D:
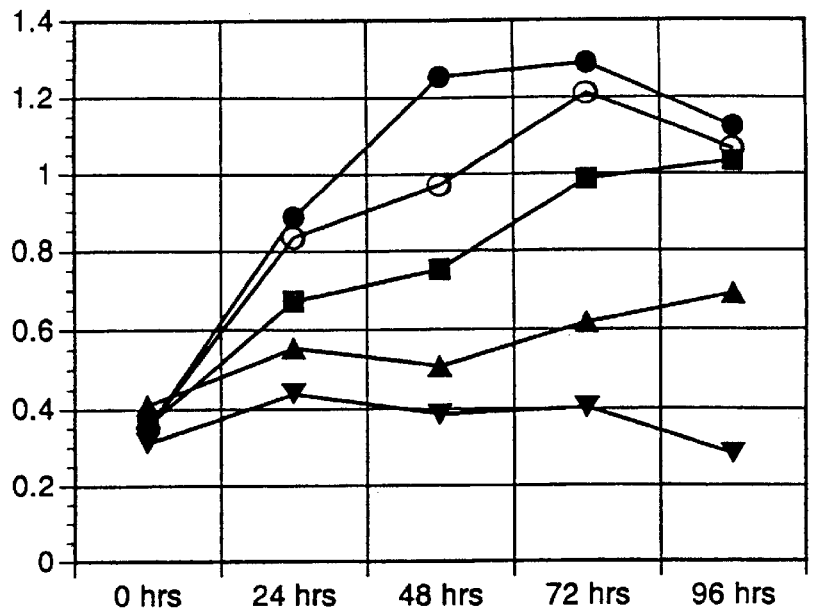

FIGS. 11A, B, C and D. FIGS. 11A and 11B: Growth curves of X-mos transformed fibroblasts at five different doxorubicin concentrations (FIG. 11A): doxorubicin=0 μM (solid circle); doxorubicin=0.025 μM (open circle); doxorubicin=0.05 μM (solid squares); doxorubicin=0.1 μM (right side up triangles); doxorubicin=0.25 μM (upside down triangles); and at five different taxol concentrations (FIG. 11B): paclitaxel=0 μM (solid circles); paclitaxel=0.5 μM (open circles); paclitaxel=1.0 μM (solid squares); paclitaxel=2.0 μM (right side up triangles); taxol=5.0 μM (upside down triangles). FIGS. 11C and 11C: Growth curves of X-mos transformed fiberblasts at five different cis-platinum concentrations (FIG. 11C): cis-platinum=0 μM (solid circles); cis-platinum=2.5 μM (open circles); cis-platinum=5.0 μM (solid squares); cis-platinum=10 μM (right side up triangles); cis-platinum=25 μM (upside down triangles); and at five different methotrexate concentrations (FIG. 11D): methotrexate=0 μM (solid circles); methotrexate=0.025 μM (open circles); methotrexate=0.05 μM (solid squares); methotrexate=0.1 μM (right side up triangles; methotrexate=0.25 μM (upside down triangles).

Figure 12A:
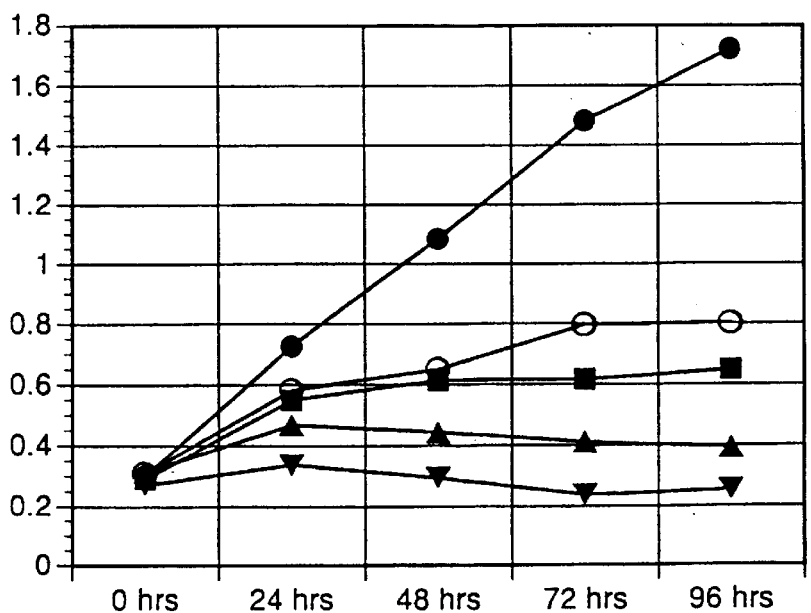
Figure 12B:
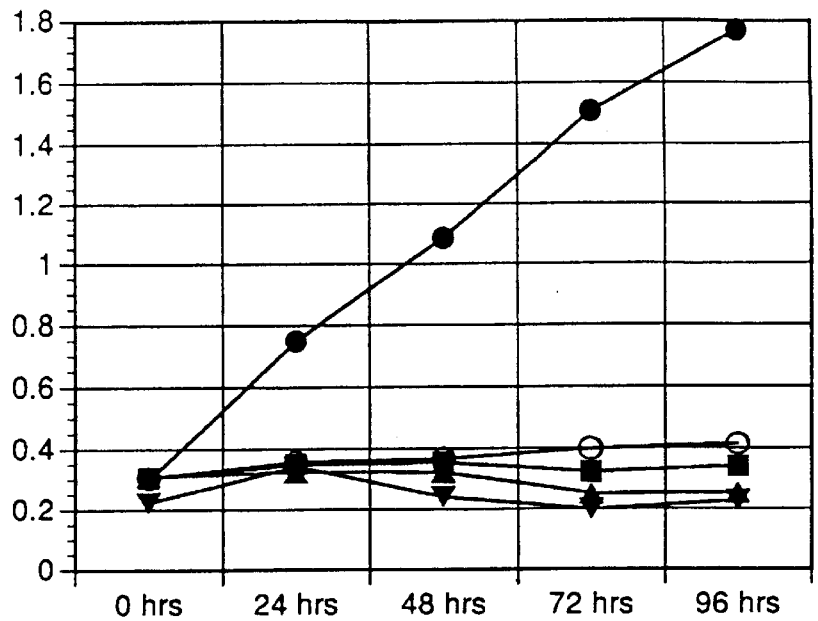
Figure 12C:
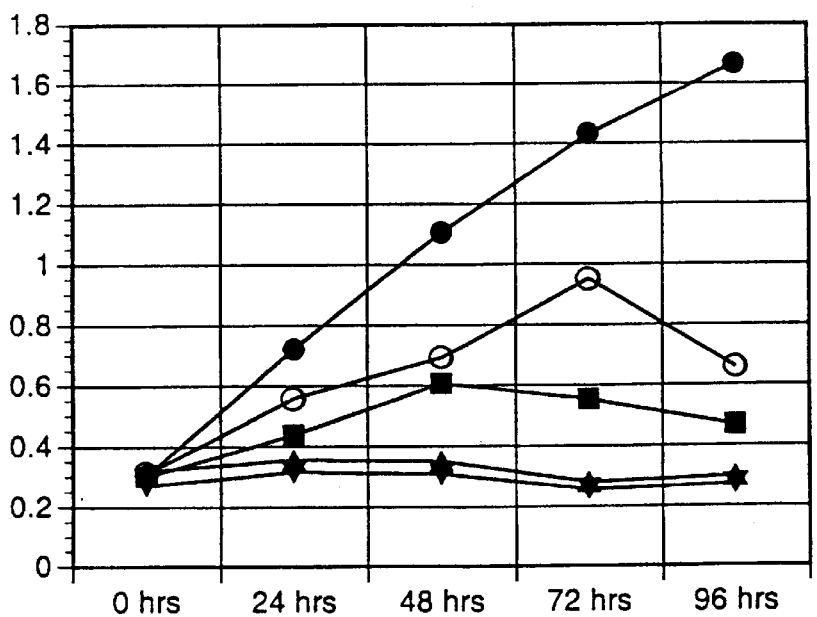
Figure 12D:
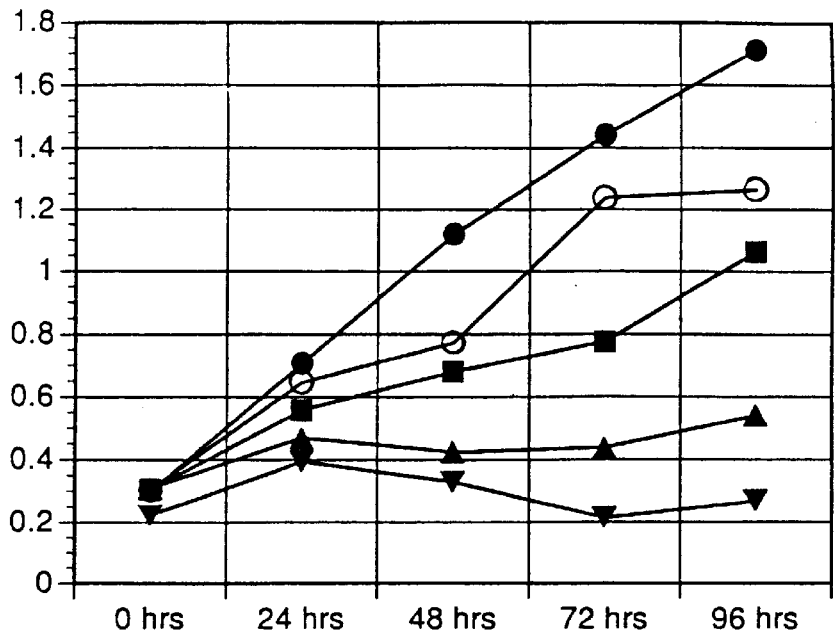

FIGS. 12A, B, C and D. FIGS. 12A and 12B: Growth curves of ras transformed fibroblasts at five different doxorubicin concentrations (FIG. 12A): doxorubicin=0 μM (solid circle); doxorubicin=0.025 μM (open circle); doxorubicin=0.05 μM (solid squares); doxorubicin=0.1 μM (right side up triangles); doxorubicin=0.25 μM (upside down triangles); and at five different paclitaxel concentrations (FIG. 12B): paclitaxel=0 μM (solid circles); paclitaxel=0.5 μM (open circles); paclitaxel=1.0 μM (solid squares); paclitaxel=2.0 μM (right side up triangles); paclitaxel=5.0 μM (upside down triangles). FIGS. 12C and 12D: Growth curves of ras transformed fibroblasts at five different cis-platinum concentrations (FIG. 12C): cis-platinum=0 μM (solid circles); cis-platinum=2.5 μM (open circles); cis-platinum=5.0 μM (solid squares); cis-platinum=10 μM (right side up triangles); cis-platinum=25 μM (upside down triangles); and at five different methotrexate concentrations (FIG. 12D): methotrexate=0 μM (solid circles); methotrexate=0.025 μM (open circles); methotrexate=0.05 μM (solid squares); methotrexate=0.1 μM (right side up triangles; methotrexate=0.25 μM (upside down triangles).

Figure 13A:
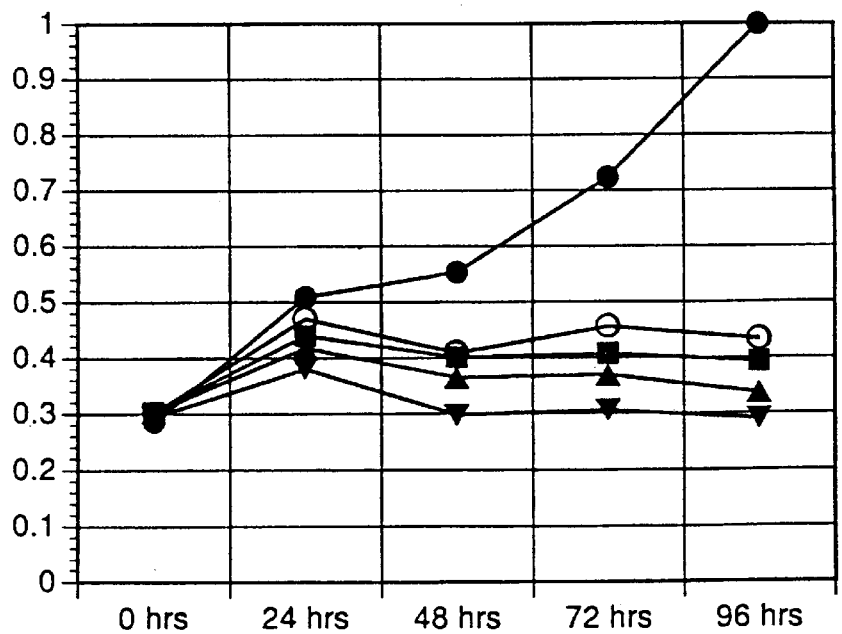
Figure 13B:
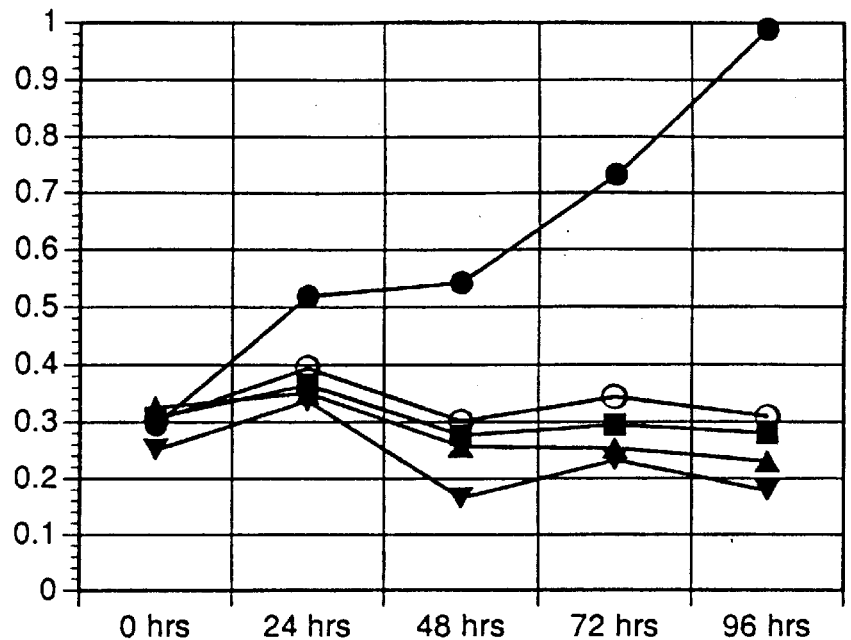
Figure 13C:
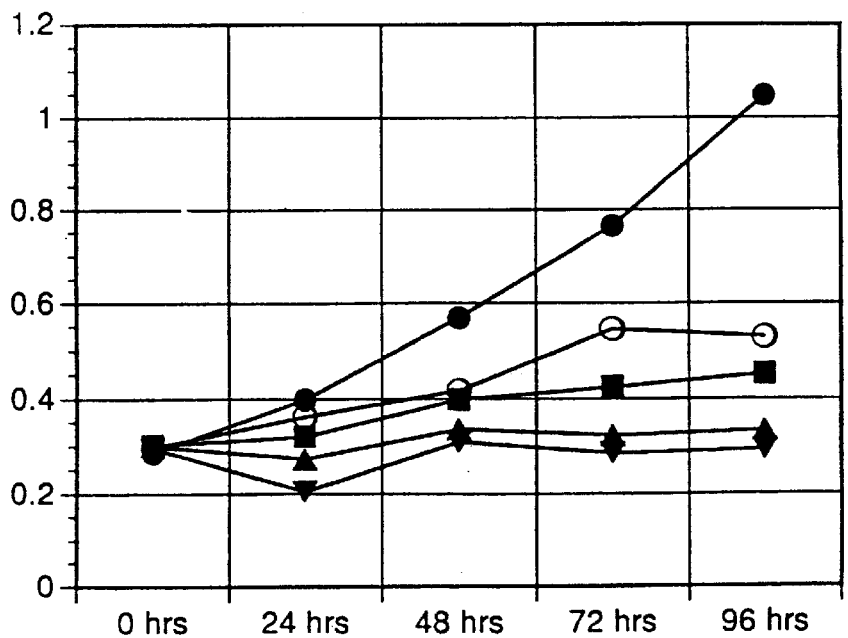
Figure 13D:
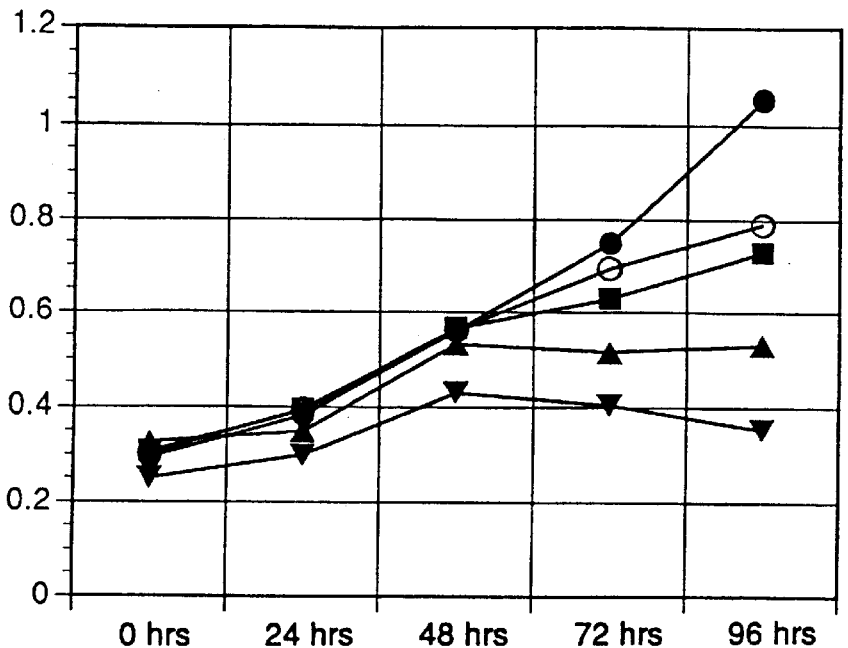

FIGS. 13A, B, C and D. FIGS. 13A and 13B: Growth curves of murine mos transformed fibroblasts at five different doxorubicin concentrations (FIG. 13A): doxorubicin=0 μM (solid circle); doxorubicin=0.025 μM (open circle); doxorubicin=0.05 μM (solid squares); doxorubicin=0.1 μM (right side up triangles); doxorubicin=0.25 μM (upside down triangles); and at five different taxol concentrations (FIG. 13B): paclitaxel=0 μM (solid circles); paclitaxel=0.5 μM (open circles); taxol=1.0 μM (solid squares); paclitaxel=2.0 μM (right side up triangles); taxol=5.0 μM (upside down triangles). FIGS. 13C and 13D: Growth curves of murine mos transformed fibroblasts at five different cis-platinum concentrations (FIG. 13C): cis-platinum=0 μM (solid circles); cis-platinum=2.5 μM (open circles); cis-platinum=5.0 μM (solid squares); cis-platinum=10 μM (right side up triangles); cis-platinum=25 μM (upside down triangles); and at five different methotrexate concentrations (FIG. 13D): methotrexate=0 μM (solid circles); methotrexate=0.025 μM (open circles); methotrexate=0.05 μM (solid squares); methotrexate=0.1 μM (right side up triangles; methotrexate=0.25 μM (upside down triangles).

Figure 14A:
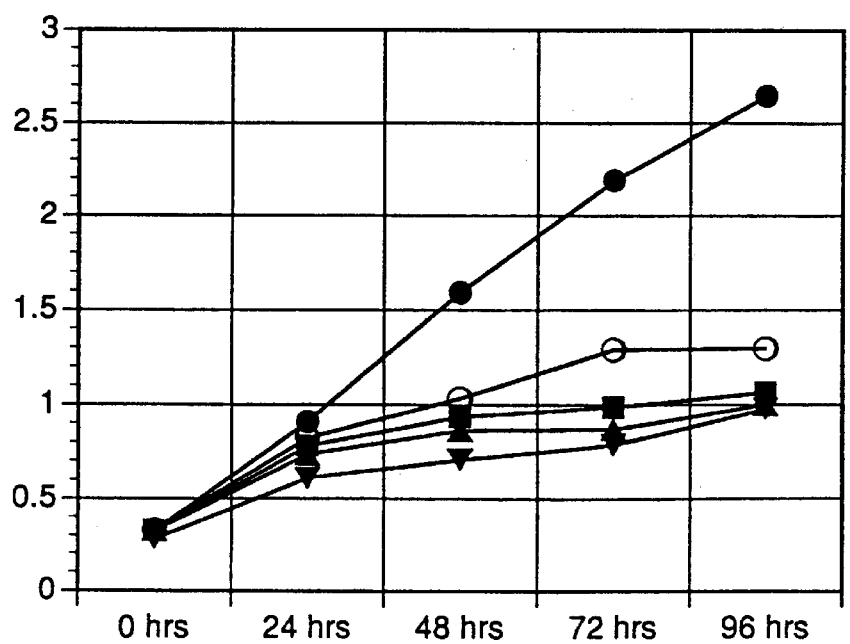
Figure 14B:
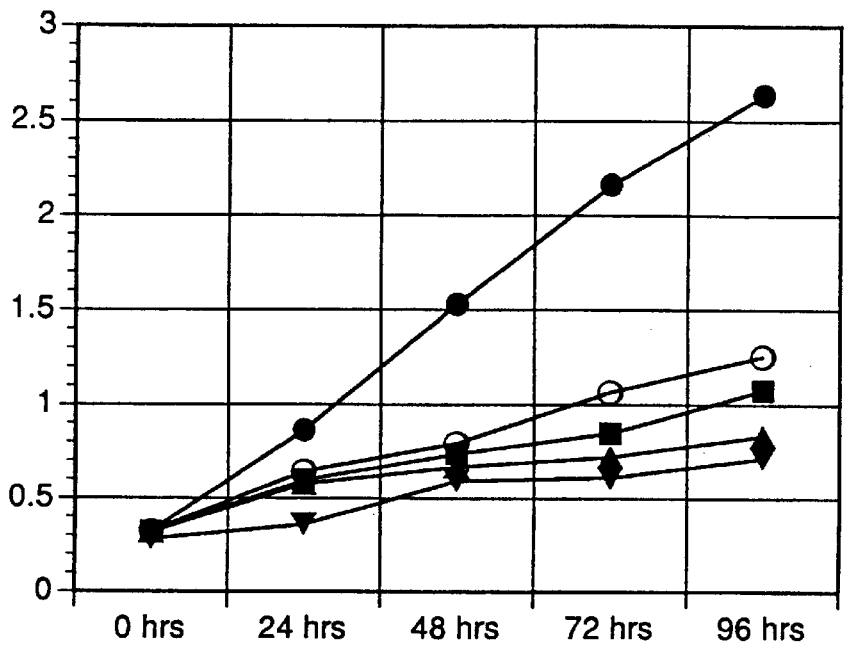
Figure 14C:
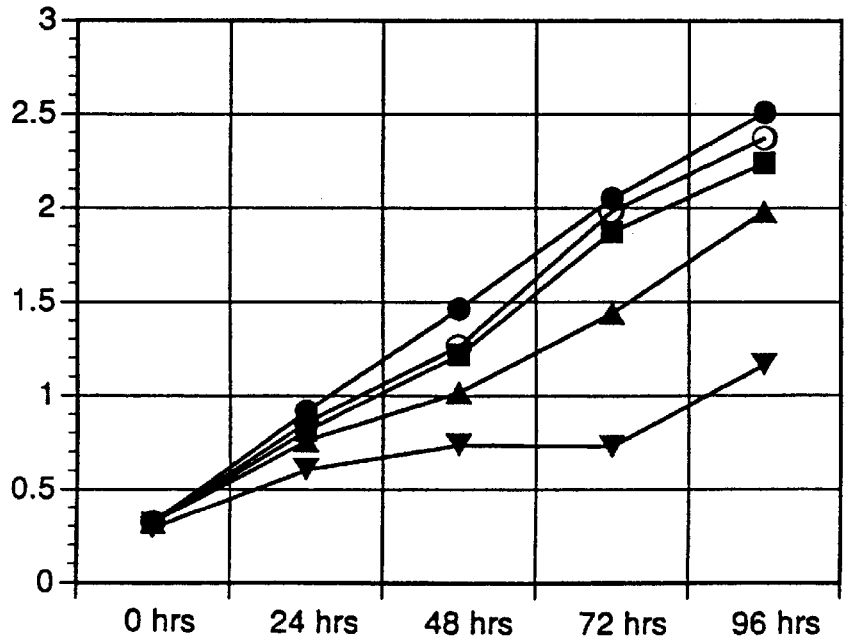
Figure 14D:
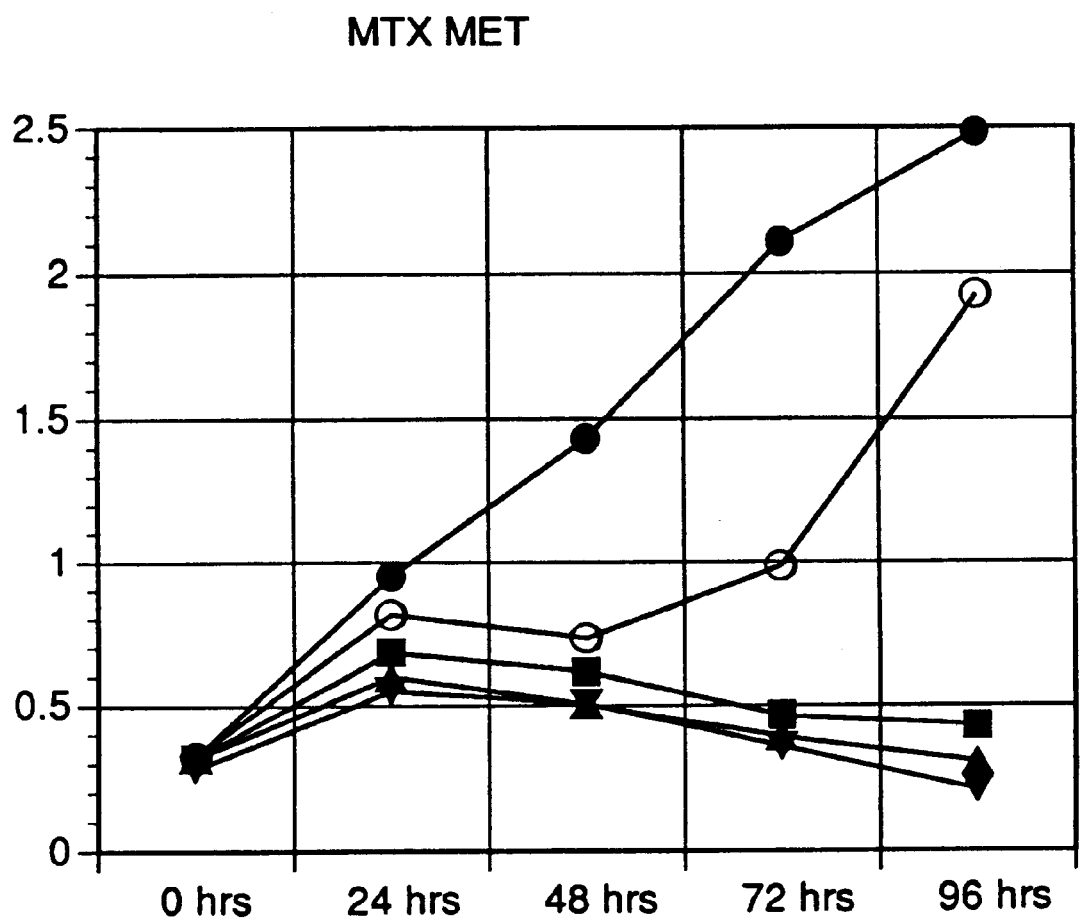

FIGS. 14A, B, C and D. FIGS. 14A and 14B: Growth curves of murine c-met transformed fibroblasts at five different doxorubicin concentrations (FIG. 14A): doxorubicin=0 μM (solid circle); doxorubicin=0.025 μM (open circle); doxorubicin=0.05 μM (solid squares); doxorubicin=0.1 μM (right side up triangles); doxorubicin=0.25 μM (upside down triangles); and at five different taxol concentrations (FIG. 14B): paclitaxel=0 μM (solid circles); paclitaxel=0.5 μM (open circles); paclitaxel=1.0 μM (solid squares); paclitaxel=2.0 μM (right side up triangles); taxol=5.0 μM (upside down triangles). FIGS. 14C and 14D: Growth curves of murine c-met transformed fibroblasts at five different cis-platinum concentrations (FIG. 14C): cis-platinum=0 μM (solid circles); cis-platinum=2.5 μM (open circles); cis-platinum=5.0 μM (solid squares); cis-platinum=10 μM (right side up triangles); cis-platinum=25 μM (upside down triangles); and at five different methotrexate concentrations (FIG. 14D): methotrexate=0 μM (solid circles); methotrexate=0.025 μM (open circles); methotrexate=0.05 μM (solid squares); methotrexate=0.1 μM (right side up triangles; methotrexate=0.25 μM (upside down triangles).

DEFINITIONS

Drug—any active agent which has a biological effect on cell growth or cell cycle including, but not limited to, traditional anticancer drugs such as those shown in Table 4, proteins having anticancer activity such as tumor necrosis factor and lymphotoxin, and proteins encoded by oncogenes or proto-oncogenes, antibodies or antibody conjugates which target cancer cells, etc.

S-phase drug—a drug which exerts its primary cytostatic or cytotoxic effect on mammalian cell cycle prior to or during S-phase.

M-phase drug—a drug which exerts its primary cytostatic or cytotoxic effect on mammalian cell cycle after S-phase but prior to or during M-phase.

Oncogene—altered form or expression of a proto-oncogene which leads to a transformed phenotype in a cell and/or tumor formation.

Proto-oncogene—a gene which regulates normal cell function.

Transformed phenotype—a phenotype which is not characteristic of a normal (non-cancerous) cell which includes loss of contact inhibition, altered morphology and loss of genetic stability.

Anaphase—the period after an egg has been fertilized and continuing until the chromosomes of the fertilized egg have pulled apart and separated.

Metaphase—the stage of mitosis or meiosis when chromosomes are aligned along the equatorial plane of the spindle.

Interphase—the state of the eukaryotic nucleus when it is not engaged in mitosis or meiosis; consists of $G_1$, S, and $G_2$ periods in cycling cells.

Prophase—the first stage of mitosis or meiosis, after DNA replication and before chromosomes align on the equatorial plane of the spindle.

DETAILED DESCRIPTION OF THE INVENTION

The inventors have postulated that the expression of mos during interphase in somatic cells selects for a level of product that does not arrest at mitosis but does result in expression of a partial M-phase phenotype. In mos-transformed cells, the altered cell morphology may equate with the cytoskeletal changes that occur normally during mitotic rounding. The loss of contact inhibition is an M-phase phenotype expressed by daughter cells during cytokinesis, since daughter cell formation is not growth arrested by contact. Genetic instability of transformed cells (Table 1) could be due to premature chromatin condensation events.

Table 1.

Properties of the Transformed Phenotype
Cellular Morphology
    Nuclear structure
    Cytoskeleton
Growth Characteristics and Cell Metabolism
    Anchorage independence and loss of contact inhibition
    Changes in extracellular matrix
    Growth factor independence
Genetic Instability A second intriguing possibility is that genetic instability reflects a failure in the cell cycle checkpoint function which has been described in yeast (Hartwell et al., Science, 246, 629–634 (1989)). These checkpoints are pauses that occur at specific points in the cell cycle for purposes of correcting errors, such as the fidelity of replicated DNA. While mutations in the checkpoint genes could result in a high frequency of mutations that lead to malignant transformation (Hartwell et al., Science, 246, 629–634 (1989)), it is proposed that activation of an oncogene that functions downstream of the checkpoint (e.g., constitutive expression of mos product) could compromise checkpoint function anywhere upstream on the cell cycle. This provides an explanation both for the genetic instability of tumor cells and for the greater sensitivity of tumor cells to chemotherapeutic agents compared to non-tumor cells.

A number of oncogenes induce morphological transformation similar to that induced by mos and may function in the same or parallel pathways. For example, we have investigated whether the ras oncogene product also has M-phase activities. This would indicate that constitutive M-phase activity proposed as an explanation for the mos-transformed phenotype may be more general. Several years ago, it was shown that the activated ras oncogene could induce meiotic maturation in Xenopus (Birchmeier et al., Cell, 43, 615–621 (1985)). We have extended these experiments and have demonstrated that the ras oncogene, like mos, also displays CSF activity (I. Daar et al., Science, 253, 74–76 (1991)). Thus, the Harvey ras oncogene product injected into cleaving blastomeres arrests cleavage at metaphase. This arrest occurs in the absence of mos product, demonstrating that parallel pathways to metaphase arrest exist (Barrett et al., Mol. Cell. Biol. 10, 310–315 (1990); I. Daar et al., Science, 253, 74–76 (1991)). Presumably, arrest at metaphase is due either to the prevention of degradation of MPF or to the induction of the expression of cyclin components of MPF (Murray et al., Nature, 339, 280–286 (1989); Murray et al., Nature 339, 275–280 (1989)). It is not clear how the ras oncoprotein induces stabilization of MPF, but it does so efficiently and this is consistent with its ability to induce meiotic maturation.

The ability of certain oncogenes to display M-phase activity has led us to speculate that the two classes of genes that participate in the cooperating oncogene assay (one class rescues cells from senescence, while the other is responsible for morphological transformation) (Table 2) may represent genes that function at the two major phases in the cell cycle. We propose that certain oncogenes facilitate entry into S-phase, while a second class contributes to morphological transformation by displaying M-phase activities during interphase (Table 2).

TABLE 2

Oncogene Complementation Groups in Rat Embryo Fibroblast Transformation Assay

| Group I Rescue from senescence | Group II Morphologic transformation |
|---|---|
| E1A | E1B |
| SV40 large T | Polyoma middle T |
| Polyoma large T | H-ras |
| c-myc | K-ras |
| N-myc | N-ras |
| p53 | |

While oncogenes have provided a common thread woven through all of the cancer research disciplines, there has been a lack of correlation with antineoplastic drugs. If oncogenes and tumor suppressor genes are the genes responsible for neoplastic transformation, then the ability of antineoplastic drugs to specifically target cancer cells versus normal cells would suggest that these drugs utilize alterations imposed by oncogenes.

There has been a sustained interest in how antineoplastic drugs connect with the cell cycle (Hellman et al., in: DeVita, Jr. et al., (eds.), Cancer: Principles and Practice of Oncology, 1st Ed., Philadelphia, JB Lippincott, 73–79 (1982)). A question we address here is how these drugs relate to the influence of oncogenes on the cancer cell. Taxol stabilizes tubulin polymers or contributes to the polymerization of tubulin. The gain in M-phase function by oncogenes should contribute toward M-phase especially if mos modifies tubulin. This suggests how paclitaxel might selectively work against certain cancer cells. It is now possible to ask whether there is a relationship between antineoplastic drug targets and oncogene product alterations of the cell cycle. We have placed a number of antineoplastic drugs as either upstream or downstream reacting compounds based on a survey of relevant literature (Table 3). The inventors recognize that the drugs may function at different stages and on multiple targets in the cell cycle.

TABLE 3

Selected Anti-neoplastic Agents

| $G_1$ + S-phase (Upstream) | M-phase (Downstream) |
|---|---|
| Tamoxifen (anti-estrogen) | Vincristine (tubulin binding) |
| Prednisone (corticosteriod) | Vinblastine (tubulin binding) |
| Decarbazine (DNA alkylation) | Paclitaxel (tubulin binding) |
| Mechlorethamine (DNA alkylation) | Doxorubicin (topoisomerase II inhibitor) |
| Cis platinum (DNA cross-linking) | Daunorubicin (topoisomerase II inhibitor) |
| Methotrexate (DNA synthesis) | Etoposide (topoisomerase II inhibitor) |
| 5'-Fluorouracil (DNA synthesis) | Bleomycin (DNA cross-linking) |
| Cytosin arabinoside (DNA synthesis) | |

The consideration of whether they function upstream or downstream in the cell cycle may have important implications in drug therapy (FIG. 4). Specifically, the possibility for tumor cells to develop drug resistance due to activation of an alternate cell cycle pathway should be less if the drug target is downstream in the cell cycle. We have suggested that drugs like DNA alkylating agents may preferentially target tumor cells over normal cells if the cell cycle checkpoint function (Hartwell et al., Science, 246, 629–634 (1989)) in tumor cells has been compromised. For example, repair of DNA alkylation would be compromised and alternations in mitotic apparatus would go unchecked. In addition, the vulnerability of tumor cells to antineoplastic drugs that target H-phase activity, like tubulin-specific agents and topoisomerase II inhibitors, might differentially recognize a gain in function due to oncogene-induced M-phase activity.

Certain antineoplastic agents are recognized to act synergistically (DeVita, Jr, Principles of Chemotherapy. in: DeVita, Jr. VT, Hellman S, Rosenberg SA (eds.), Cancer: Principles and Practice of Oncolocy, 1st edition, Philadelphia, JB Lippincott, 132–155 (1982)). The metabolic basis of synergy, for example, between 5 fluorouracil and methotrexate is understood (Cadman et al., Science, 50, 711–716 (1984)). The cause of synergy between other drugs, however, is not so clear. Certain drugs can be assigned as having chiefly S-phase or M-phase activity, and a possible explanation emerges regarding their synergistic action. Agents acting on targets that are sequential in the cell cycle would be expected to act in synergy: an agent that acts in S-phase might be expected to synergize with M-phase agents. Using this rationale, many chemotherapeutic protocols can be shown to be combinations of S-phase and M-phase agents (Table 4).

TABLE 4

Selected Chemotherapeutic Regimens

| Malignancy | $G_1$ or S-phase (Upstream) | M-phase (Downstream) |
|---|---|---|
| Acute Lymphocytic Leukemia | Prednisone<br>L-Asparaginase<br>Cytosine Arabinoside | Vincristine<br>Daunorubicin<br>Etoposide |
| Acute Nonlymphocytic Leukemia | Cytosine Arabinoside | Daunorubicin |
| Testicular Cancer | Cis Platinum | Bleomycin<br>Vinblastine or<br>Etoposide |
| Hodgkins Lymphoma | Mechlorethamine<br>Procarbazine<br>Prednisone | Vincristine |
|  | Dacarbazine | Doxorubicin<br>Vincristine<br>Bleomycin |

For example, acute non-lymphocytic leukemia, testicular cancer, and Hodgkins lymphoma are tumors that are treated with drugs from both categories. Further, the preponderance of either S-phase or M-phase agents in MOPP and ABVD regimens for Hodgkins lymphoma might explain the efficacy of one drug regimen as salvage chemotherapy after the other has failed.

SRB growth curve assays may be performed by plating 3T3 mouse fibroblasts at a suitable concentration, preferably 50,000 per ml, in microtiter plates, preferably 96 well microtiter plates (Falcon). The cells are then allowed to attach, preferably overnight, before exposure to various concentrations of chemotherapeutic agents. The plates can be fixed and stained with 0.4% sulforhodamine at 24, 48, 72 and 96 hours according to published protocols (JNCI). Preferably, multiple runs are performed to obtain data in quadruplicate.

The inventors have discovered that the growth of oncogene-transformed cells may be completely inhibited by the combination of a drug having S-phase actvity and a subtherapeutic effect of a drug having M-phase activity. For example, SRB growth curve assays indicate that cis-platinum in combination with a subtherapeutic amount of taxol completely inhibits the growth of X-mos transformed cells and Mu-met transformed cells, while cis-platinum alone only moderately inhibited the growth of the oncogene-transformed cells (FIGS. 7, 8). Thus, drugs in amounts which alone do not essentially result in the complete inhibition of oncogene-transformed cell growth may exhibit a synergistic effect in combination which does result in the complete inhibition of oncogene-transformed cell growth. These findings also suggest that the SRB assay may be useful for predicting clinical drug synergy because there appears to be a tie-in to oncogenic activation.

Knowing where oncogenes function in the cell cycle can be used not only to elucidate mechanisms for currently used drugs, but also may aid the design of drugs in the future.

The inventors have tried to explain interactions between cell cycle, oncogenes and antineoplastic drugs. The studies we discuss suggest a direct link between oncogene, cell cycle activity, and antineoplastic drugs. The vulnerability of certain cancers to the empirically established chemotherapeutic protocols may be related to the oncogene activated and its influence on the cell cycle.

The inventors have discovered that cells transformed with certain oncogenes are more sensitive to chemotherapeutic agents than the parental cell line. Furthermore, different oncogenes confer differential sensitivities to various agents (FIGS. 10–14). The correlation between the different oncogenes and their sensitivities to different chemotherapeutic agents may aid in designing new chemotherapeutic combinations and agents and predicting which human cell lines with known activated oncogenes are sensitive to which agents or combinations of agents.

The inventors have discovered that the mos proto-oncogene product is an essential component of cytostatic factor (CSF), which has been shown to directly or indirectly stabilize MPF (Sagata et al., *Nature*, 342, 512–518 (1989); Gerhart et al., *J. Cell Biol.*, 98, 1247–1255 (1984); Newport et al., *Cell*, 30, 675–686 (1984); Murray et al., *Nature*, 339, 280–286 (1989)).

The inventors have shown that the mos proto-oncogene product functions during M-phase (Sagata et al., *Nature*, 342, 512–518 (1989); Sagata et al., *Nature*, 335, 519–525 (1988); Sagata et al., *Science*, 245, 643–646 (1989); Paules et al., *Proc. Natl. Acad. Sci. USA*, 86, 5395–5399 (1989)). Our findings led us to propose that the phenotype of cells transformed by mos and by certain other oncogenes that display M-phase activity may be due to the expression of M-phase events during interphase (Sagata et al., *Nature*, 342, 512–518 (1989); Sagata et al., *Nature*, 335, 519–525 (1988); Sagata et al., *Science*, 245, 643–646 (1989)). Shalloway and co-workers have arrived at similar conclusions regarding src transforming activity (Chackalaparampil et al., *Cell*, 801–810 (1988)).

Figure 1:
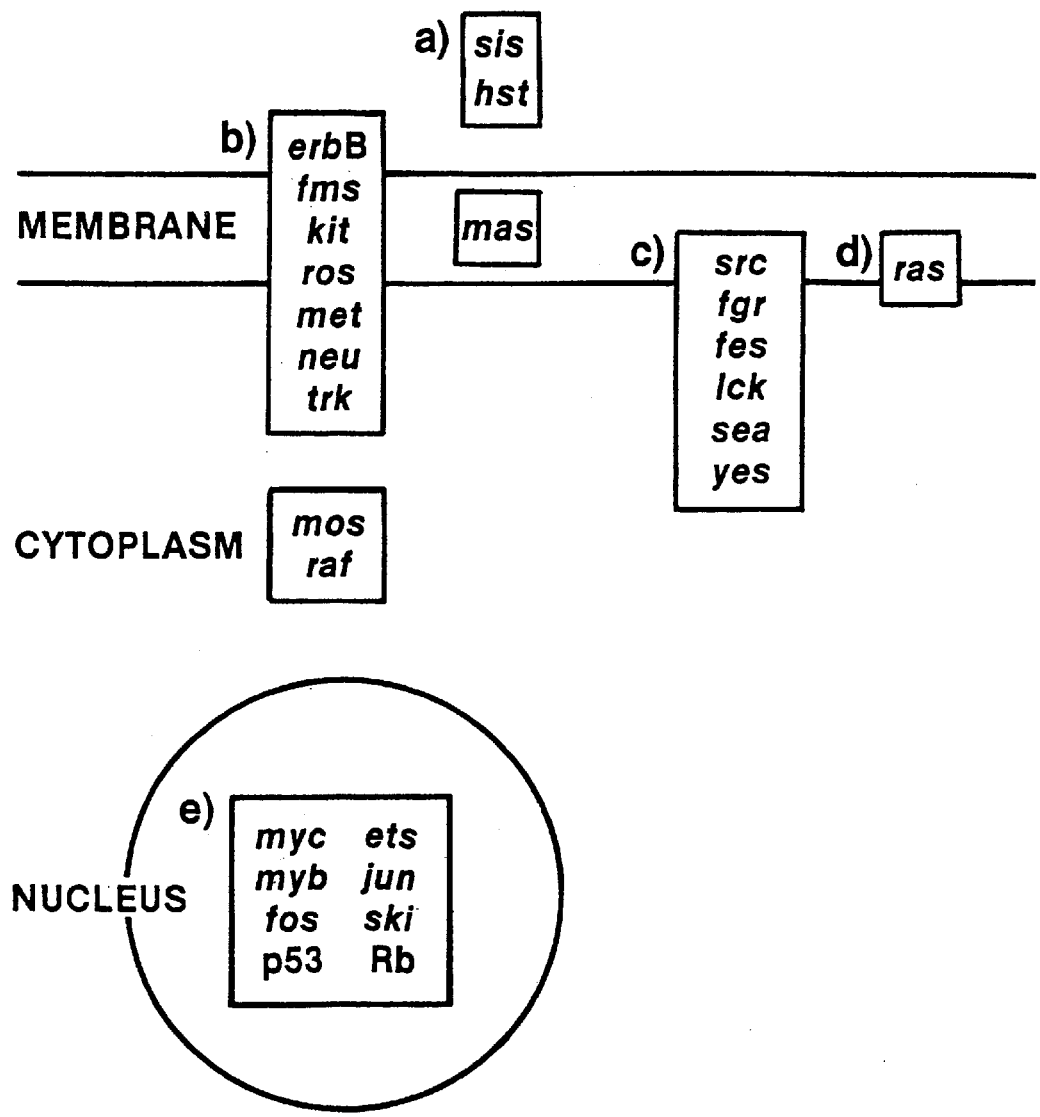
FIG. 1. Cellular localization of oncogene, proto-oncogene, and tumor suppressor gene products. Depicted are certain members of each oncogene family: growth factors (external mitogenic signals) (a); transmembrane tyrosine kinase growth factor receptors (b); nonintegral membrane-associated proteins of the src gene family (c) and ras gene family (d); and oncogene products localized in the nucleus (e).
Figure 2:
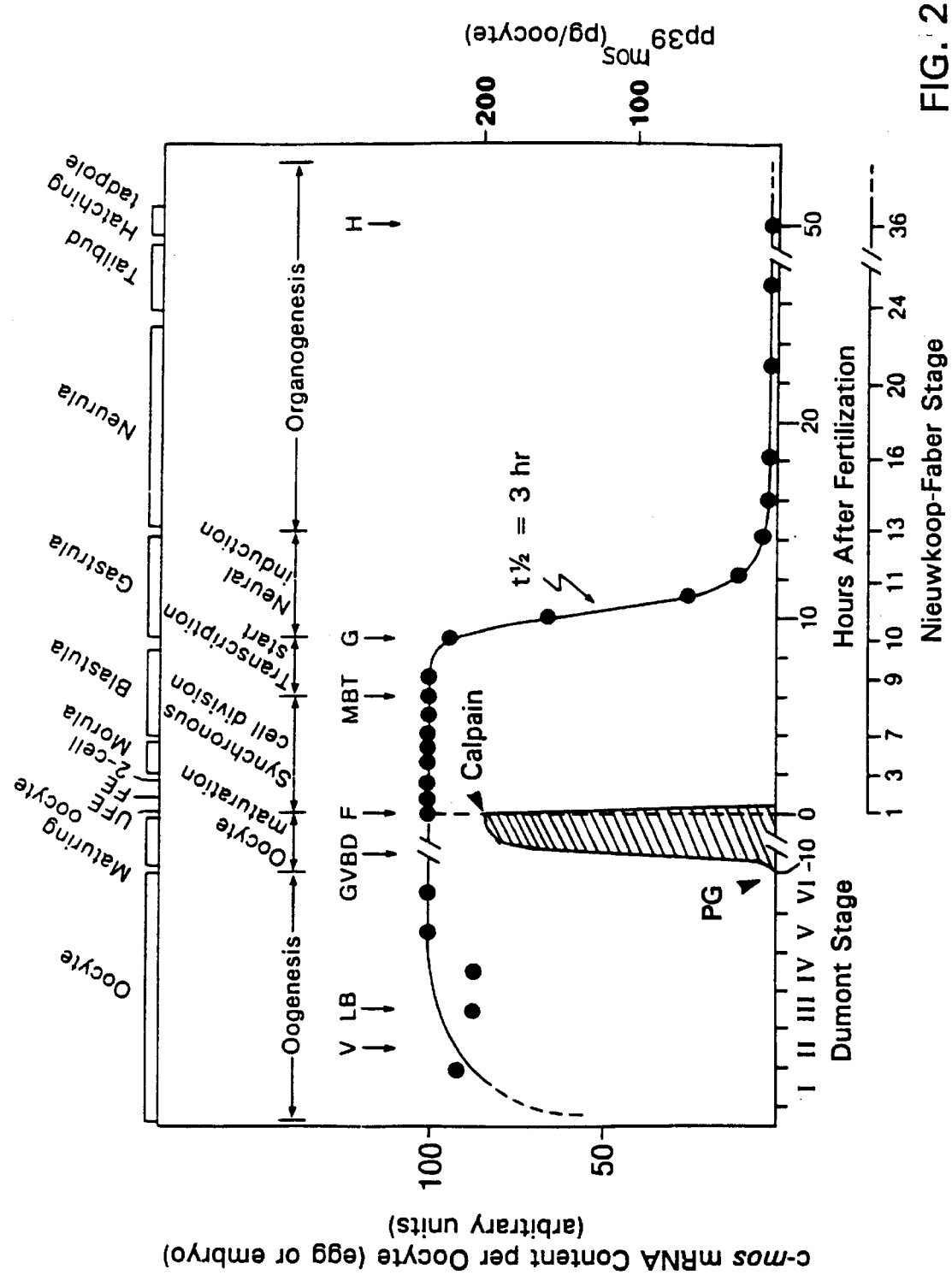
FIG. 2. Expression patterns of c-mos RNA and Mos protein (pp39$^{mos}$) during early development of *Xenopus*

It is very likely that understanding the normal function of cellular proto-oncogenes will reveal how these genes transform cells. The mos proto-oncogene was discovered as the transforming gene of the acute transforming retrovirus that was captured from the host genome during virus replication (Frankel et al., *J. Virol.*, 21, 153–160 (1977); Jones et al., *Proc. Natl. Acad. Sci. USA*, 77, 2651–2655 (1980); Oskarsson et al., *Science*, 207, 1222–1224 (1980)). A breakthrough in understanding its normal function came with the discovery that the gene was specifically expressed in germ cells during normal development (Propst et al., *Nature*, 315, 516–518 (1985)). Early development in *Xenopus laevis* is well characterized, and by using this system we discovered that the ros product was expressed only during meiosis (Sagata et al., *Nature*, 335, 519–525 (1988); Sagata et al., *Science*, 245, 643–646 (1989)) (FIG. 2). This provided the opportunity to test whether mos was required for oocyte maturation.

In Xenopus, oocyte maturation in vivo as well as in vitro is induced by progesterone. We have shown that $pp39^{mos}$ is required for progesterone-induced Xenopus oocyte maturation by injecting fully grown oocytes with mos antisense oligodeoxyribonucleotides (Sagata et al., *Nature*, 335, 519–525 (1988)). Oocyte maturation, as evidenced by breakdown of the germinal vesicle (GVBD), is completely blocked when $pp39^{mos}$ expression is depleted. This loss of mos function is the antithesis of the transformed phenotype produced by the constitutively expressed mos oncogene in somatic cells where it represents a gain of function.

Studies by Watanabe et al. (*Nature*, 342, 505–511 (1989)) indicated that even though the mos product was stable in unfertilized eggs, or mature oocytes, within 30 minutes after fertilization all $pp39^{mos}$ disappeared (FIG. 2) (*Nature*, 342, 505–511 (1989)). This rapid disappearance of mos after egg activation with a calcium ionophore (a process akin to fertilization) was explained by showing that mos is specifically degraded by calpain, a calcium-dependent cysteine protease (*Nature*, 342, 505–511 (1989)).

Figure 3B:
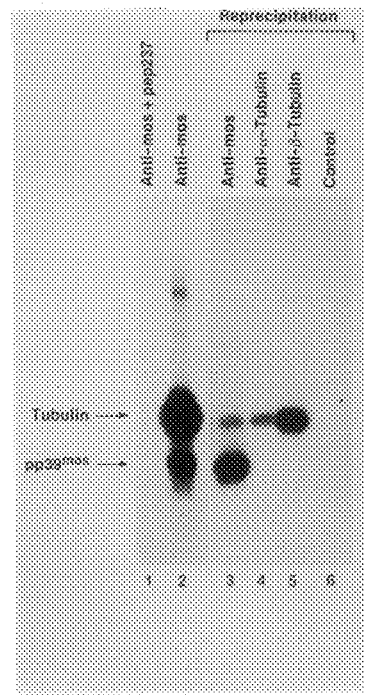
Figure 3C:
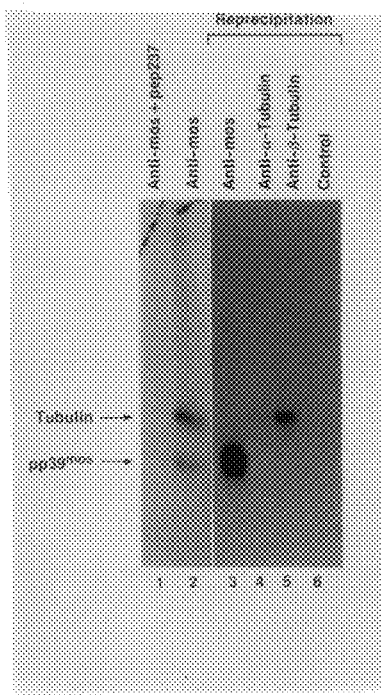

Calcium sensitivity and rapid degradation of mos product after fertilization are properties of CSF (Meyerhof et al., Dev. Biol., 61, 214–229 (1977)). CSF, an activity present in mature oocytes, was first characterized by Masui and Markert (Masui et al., J. Exp. Zool., 177, 129–146 (1971)) and is believed to be responsible for arresting vertebrate oocytes at metaphase II of meiosis. Masui and Markert (Masui et al., J. Exp. Zool., 177, 129–146 (1971)) showed that CSF injected into a blastomere of a cleaving embryo arrests it at metaphase of mitosis. Similarly, when mos RNA was injected into one cell of a two-cell embryo, cleavage was arrested at metaphase in the injected blastomere (Sagata et al., Nature, 342, 512–518 (1989)) (FIG. 3). Moreover, antibodies directed against mos can eliminate CSF activity prepared from unfertilized eggs (Sagata et al., Nature, 342, 512–518 (1989)). Thus, pp39$^{mos}$ is active in arresting oocytes at metaphase II of meiosis. This phase is considered to be a major cell cycle control point and is where the highest levels of MPF are found (Murray et al., Science, 246, 614–621 (1989)). CSF directly or indirectly stabilizes MPF (Sagata et al., Nature, 342, 512–518 (1989); Gerhart et al., J. Cell Biol., 98, 1247–1255 (1984); Newport et al., Cell, 30, 675–686 (1984); Murray et al., Nature, 339, 280–286 (1989)). The mos product, as an active component of CSF, provides a direct link between proto-oncogene activity and the cell cycle regulators p34$^{cdc2}$ and cyclin.

The inventors' recent focus has been to identify what CSF represents and to characterize the biochemical properties of the mos product. The mos product is required throughout maturation in both mouse (Paules et al., Proc. Natl. Acad. Sci. USA, 86, 5395–5399 (1989); O'Keefe et al., Dev. Biol., 60, 7038–7042 (1989)) and Xenopus oocytes (Sagata et al., Nature, 335, 519–525 (1988)), and its depletion results in the arrest of the process. As mentioned above, such oocytes lack MPF (Sagata et al., Science, 245, 643–646 (1989)). Depleting mos product in mouse oocytes undergoing meiotic maturation blocked development in metaphase I at a specific morphogenetic stage. These studies provided the first indication where mos might function (Paules et al., Proc. Natl. Acad. Sci. USA, 86, 5395–5399 (1989)). Mouse oocytes mature in vitro to unfertilized eggs, as is evidenced by the emission of the first polar body (FIG. 4). In the right panel, the mos product has been eliminated by destroying the endogenous nos RNA (Paules et al., Proc. Natl. Acad. Sci. USA, 86, 5395–5399 (1989)) and maturation is interrupted at the point where the mos product is required. In maturing mouse oocytes depleted of endogenous mos, GVBD occurs as does chromosome condensation. Both activities are attributed to MPF (Lohka et al., J. Cell Biol., 98, 1222–1230 (1984); Lohka et al., J. Cell Biol., 101, 518–523 (1985); Miake-Lye et al., Cell, 41, 165–175 (1985)). Microtubule-mediated cytoplasmic organelle transport, however, is interrupted following GVBD (Paules et al., Proc. Natl. Acad. Sci. USA, 86, 5395–5399 (1989)), indicating that mos is required for this process. This suggests that mos may be involved in microtubule modification. Additional evidence that pos may have a microtubule-related activity is that blastomeres arrested by CSF were shown by Meyerhof and Masui (Meyerhof et al., Dev. Biol., 80, 489–494 (1979)) to have a larger than normal mitotic spindle. Moreover, taxol, a microtubule-stabilizing and tubulin-polymerizing antineoplastic drug (Schiff et al., Proc. Natl. Acad. Sci. USA, 77, 1561–1565 (1980); Schiff et al., Nature, 277, 665–667 (1979)), mimics CSF/mos in blastomeres (Heidemann et al., Dev. Biol., 80, p. 489 (1980)). The following analyses of pp39$^{mos}$ in vitro and in vivo are consistent with a role in microtubule modification.

The following examples further illustrate the present invention but, of course, should not be construed as in any way limiting its scope.

EXAMPLE 1

The inventors have found that in vitro mos product is associated with and phosphorylates tubulin (Zhou et al., Science, 251 671–675 (1991)). Thus, mos product immunoprecipitated from transformed cells metabolically labeled with methionine shows a band with the mobility of tubulin (FIG. 3). An equivalent precipitate, eluted and reprecipitated with tubulin antibodies shows that both α- and β-tubulin are present. The same analyses performed on unlabeled extracts from either transformed cells or from unfertilized Xenopus eggs, and subjected in vitro to phosphorylation by mos kinase, show that both pp392$^{mos}$ and tubulin are phosphorylated (FIG. 3). These analyses indicate that β-tubulin is preferentially precipitated and phosphorylated in extracts from either cells transformed by the Xenopus mos product or by the endogenous mos product in unfertilized eggs.

By immunofluorescence analysis the mos product in transformed cells also colocalizes with tubulin at the metaphase spindle pole. In early telophase, mos protein colocalizes with tubulin in the mid-body and aster that becomes the new microtubule-organizing center of the daughter cells.

The mos product may function to modify microtubules and contribute to the formation of the spindle. The appearance of the mos product during meiosis coincides with both formation of the spindle and stabilization of MPF at metaphase II of meiosis (Sagata et al., Science, 245, 643–646 (1989); Watanabe et al., Nature, 342, 505–511 (1989)). After fertilization, mos proteolysis occurs concomitantly with poleward migration of chromosomes at anaphase. In our model, pp39$^{mos}$ contribution to the spindle results in metaphase arrest, and its loss is associated with chromosome migration. An interesting possibility is that during interphase, a limited modification of microtubules by mos product may be responsible for the transformed phenotype. Alternatively, it is possible that the association of pp39$^{mos}$ with microtubules provides a vehicle to direct the kinase to specific substrates. This would allow B2 cyclin to be a potential substrate for pp39$^{mos}$ (Roy et al., Cell, 61, 825–831 (1990)). Although, in mos-transformed cells, MPF is not present during G$_1$ and S-phases

EXAMPLE 2

In the Xenopus laevis system, fully grown oocytes are arrested in prophase of the first meiotic division. Progesterone releases this arrest, resulting in the activation of M-phase promoting factor (MPF), germinal vesicle breakdown (GVBD), the completion of meiosis I, and the production of an unfertilized egg arrested at metaphase II of meiosis (Y. Masui et al., Int. Rev. Cytol., 57, 185 (1979)). MPF is comprised of the Xenopus homolog of the cell cycle regulator p34$^{cdc2}$ and cyclin (J. Gautier et al., Cell, 54, 433 (1988); W. G. Dunphy et al., Cell, 54, 423 (1988); J. Gautier et al., Cell, 60, 487 (1990)), and is present at high levels in unfertilized eggs (Y. Masui et al., Int. Rev. Cytol., 57, 185 (1979)). Cytostatic factor (CSF) is also found in unfertilized eggs and is believed to be responsible for the arrest of maturation at metaphase II of meiosis (Y. Masui et al., Int. Rev. Cytol., 57, 185 (1979); J. W. Newport et al., Cell, 37, 731 (1984)). The mos proto-oncogene product has been shown to be an active component of CSF, and introduction of CSF or mos into blastomeres of rapidly cleaving embryos arrests cleavage at metaphase of mitosis (Y. Masui et al., Int. Rev. cytol., 57, 185 (1979); J. W. Newport et al., Cell, 37, 731 (1984); N. Sagata et al., Nature, 342, 512 (1989)). This arrest by CSF or mos, at a major cell cycle control point (A.

W. Murray et al., *Science*, 246, 614 (1989)), results from the stabilization of high levels of MPF (J. W. Newport et al., *Cell*, 37, 731 (1984); N. Sagata et al., *Nature*, 342, 512 (1989); J. Gerhart et al., *J. Cell Biol.*, 98, 1247 (1984); A. W. Murray et al., *Nature*, 339, 280 (1989)).

The unrestricted proliferation of cells transformed by oncogenes provides a strong argument that proto-oncogenes normally function in the regulation of the cell cycle (M. Park et al., *The Metabolic Basis of Inherited Disease*, Vol. 1, E. R. Scriver, A. L. Beaudet, W. S. Sly, and D. Valle, Eds. (McGraw-Hill, New York, 1989), p. 251). Major research emphasis has been directed toward understanding how oncogenes alter the regulation of signal transduction events in the $G_0$ to $G_1$ phase of the cell cycle (A. B. Pardee, *Science*, 246, 603 (1989)). The discovery that the mos proto-oncogene product functions during M-phase (N. Sagata et al., *Nature*, 342, 512 (1989); N. Sagata et al., *Nature*, 335, 519 (1988)) led us to propose that the transforming activity of the mos product in somatic cells is due to the expression of its M-phase activity during interphase (N. sagata et al., *Nature*, 342, 512 (1989); N. Sagata et al., *Nature*, 335, 519 (1988); N. Sagata et al., *Science*, 245, 643 (1989)). A similar hypothesis has been presented for the src transforming activity (I. Chaklalaparampil et al., *Cell*, 52, 801 (1988)) and this may be a more general mechanism for how certain oncogenes induce morphological transformation (N. Sagata et al., *Nature*, 342, 512 (1989); N. Sagata et al., *Nature*, 335, 519 (1988); N. Sagata et al., *Science*, 245 643 (1989)). In this report, we show that the ras oncoprotein, the paradigm of transforming GTP-binding proteins (M. Barbacid, *Annu. Rev. Biochem.*, 56, 779 (1987)) also has M-phase activity.

The ras oncoprotein, p21, and the inos proto-oncogene product, $pp39^{mos}$, induce progesterone-independent meiotic maturation in Xenopus oocytes (N. Sagata et al., *Science*, 245 643 (1989); C. Birchmeier et al., *Cell*, 43, 615 (1985); C. B. Barrett et al., *Mol. Cell. Biol.*, 10, 310 (1990); C. C. Allende et al., *FEBS Lett.*, 234, 426 (1988); R. S. Freeman et al., *Proc. Natl. Acad. Sci. U.S.A.*, 86 5805 (1989)) (Table 1). We tested the ras oncogene product in this assay by injecting either the ras oncoprotein or H-ras$^{val12}$ RNA. Injected oocytes were subsequently examined for GVBD and MPF activity. Cloned Xenopus mos was inserted into the Sac I restriction site of a modified pTZ18 vector having a polyA tail. The H-ras$^{val12}$ cDNA was ligated into the Sal I and Bam HI restriction sites of the SP64 vector (Promega). All RNAs were capped and transcribed by the method recommended by the supplier (Stratagene) using either T7 or SP6 RNA polymerase. ras$^{lys12}$ p21 proteins were purified as described in Hayag et al., *Oncogene*, 5, 1481 (1990). Crude MPF extracts were prepared as previously described in Sagata et al., *Science*, 245, 643 (1989). Briefly, groups of 10 to 20 oocytes were homogenized in 20 to 40 µl of MPF extract buffer [80 mM sodium β-glycerophosphate (Sigma), 20 mM EGTA, 15 mM $MgCl_2$, 20 mM Hepes (pH 7.2), 1 mM ATP (Boehringer Mannheim) and 5 mM sodium fluoride]. The homogenate was centrifuged at 16,000×g for 5 min at 4° C., and the supernatant was used for microinjections. Groups of 10 to 20 oocytes were incubated in MBS (Durkin et al., *Mol. Cell. Biol.*, 7, 444 (1987)) containing cycloheximide (10 µg/ml; Sigma) for 1 hour and then injected with 40 nl of the supernatant from each appropriate donor group. After 2 to 3 hours of culturing the oocytes in the presence of cycloheximide, we examined recipient oocytes for GVBD. Cytosolic extracts prepared from oocytes induced to mature with these products were positive for MPF, indicating that the oocytes were arrested in metaphase (Table 5).

TABLE 5

Influence of oncogene products on oocyte maturation in the presence or absence of $pp^{39mos}$.

| Treatment or Injection | Amount (ng/oocyte) | Pretreatment‡ | Assays | Injected oocytes | w/GVBD | % GVBD ± SD | MPF activity |
|---|---|---|---|---|---|---|---|
| Progesterone |  | S | 12 | 125 | 104 | 83 ± 14 | + |
|  |  | AS | 12 | 145 | 16 | 11 ± 7 | − |
| H-ras$^{Val12}$ RNA | 1 | -- | 2 | 20 | 12 | 60 | N.D. |
|  | 5 | -- | 2 | 23 | 22 | 96 | N.D. |
|  | 10 | B | 8 | 80 | 74 | 93 | + |
|  | 10 | S | 8 | 130 | 112 | 86 ± 15 | + |
|  | 10 | AS | 8 | 130 | 78 | 60 ± 20 | +* |
| H-ras$^{Lys12}$ p21 | 15 | B | 8 | 80 | 72 | 90 | + |
|  | 15 | S | 8 | 194 | 170 | 88 ± 8 | + |
|  | 15 | AS | 8 | 202 | 107 | 52 ± 22 | +* |
| C-mos$^{XO}$ RNA | 1 | -- | 1 | 20 | 1 | 5 | n.d. |
|  | 50 | -- | 1 | 10 | 10 | 100 | + |

‡ - B (buffer); S (sense) or AS (antisence) oligodeoxyribonucleotides; 120 ng of oligodeoxyribonucleotides were injected per oocyte; -- (no pretreatment).
\* - Only oocytes displaying GVBD were used in MPF assay.
n.d. - not determined.
SD - standard deviation.

The following procedure was utilized to obtain the data set forth in Table 5 concerning the influence of the ras oncogene products on oocyte maturation in the presence or absence of pp39$^{mos}$. *Xenopus laevis* females were obtained from Xenopus I (Ann Arbor, Mich.). Oocytes were removed from the surrounding follicle tissue by the addition of modified Barth solution (MBS) containing collagenase A (2 mg/ml; Boehringer Mannheim) (Durkin et al., *Mol. Cell. Biol.*, 7, 444 (1987)) and incubated for 2 hours. The oocytes were washed extensively with MBS, and stage VI (Dunmont, *J. Morphol.*, 136, 153 (1972)) oocytes were removed and allowed to recover overnight. Groups of 10 to 30 oocytes were microinjected using an Attocyte injector (ATTO Instruments) with 40 nl of the appropriate reagent diluted to the desired concentration in 88 mM NaCl and 15 mM Tris (pH 7.5). In the cases where mos sense or antisense oligodeoxyribonucleotides [described as A to D by Sagata et al., *Nature*, 335, 519 (1989)] were used in injections, oocytes were cultured for 3.5 to 4 hours before the second indicated treatment or injection. GVBD was determined 14 to 18 hours later by the appearance of a white spot at the animal pole. In addition, all oocytes were soaked in 10% trichloroacetic acid for 10 min, then dissected and examined under a binocular microscope for the presence or absence of the germinal vesicle. Oocytes were scored for GVBD 14 to 18 hours later. Where indicated, MPF activity was tested and denoted by (+) where activity was found, by (−) where none was observed, and by (ND) where activity was not determined.

In addition, these analyses confirm that the ras oncoprotein (A. K. Desphande et al., *Mol. Cell. Biol.*, 7, 1285 (1987)), like the mos product, can sustain high levels of MPF after GVBD (Table 5).

In fully grown Xenopus oocytes, antisense oligodeoxyribonucleotides destabilize the mos maternal RNA and block progesterone-induced meiotic maturation (N. Sagata et al., *Nature*, 335, 519 (1988); C. B. Barrett et al., *Mol. Cell. Biol.*, 10, 310 (1990)). To test whether the ras oncoprotein could induce meiotic maturation in the absence of progesterone and endogenous mos MRNA, we injected mos-specific antisense or sense oligodeoxyribonucleotides (N. Sagata et al., *Nature*, 335, 519 (1988)) into oocytes 3.5 to 4 hours before injecting the test material and subsequently examined them for GVBD and MPF activity (Table 5). This assay showed that GVBD occurred frequently in mos-minus oocytes injected with the ras oncogene (60%), and extracts prepared from oocytes displaying GVBD were positive for HPF activity (Table 5). Barrett and co-workers have shown that mos depletion inhibits ras-induced maturation (15). Allende and co-workers reported that the ras oncogene product can induce GVBD in cycloheximide-treated oocytes (C. C. Allende et al., *FEBS Lett.*, 234, 426 (1988)) and Barrett also observed this occasionally (C. B. Barrett et al., *Mol. Cell. Biol.*, 10, 310 (1990)). These latter results are more consistent with our data, since pp39$^{mos}$ not synthesized in oocytes in the presence of cycloheximide (N. Sagata et al., *Science*, 245, 643 (1989); N. Watanabe et al., *Nature*, 342, 505 (1989)). Moreover, ras-induced oocyte maturation appears to be mos dependent in less mature Dumont stage V (J. N. Dumont, *J. Morphol.*, 136, 153 (1972) oocytes but not in fully grown stage VI oocytes, presumably due to metabolic changes during oogenesis.

Since the ras oncoprotein induces meiotic maturation and high levels of MPF in oocytes, we tested whether it influences M-phase events in cleaving embryos where the cell cycle consists essentially of S- and M-phases. Strikingly, the ras oncoprotein efficiently arrested embryonic cleavage when one blastomere of each 2-cell embryo was injected with either oncogenic ras p21 or RNA. This cleavage arrest mimics the arrest caused by CSF or the mos product (N. Sagata et al., *Nature*, 342, 512 (1989)) and is a new activity for the oncoprotein. Moreover, as little as 1 to 2 ng of ras oncogene product can induce the cleavage arrest, which is observable within a few hours.

While the ras oncoprotein induced the cessation of embryonic cleavage, both normal and nontransforming mutant forms of the ras oncoprotein had no observable effect on cleavage, even when introduced at concentrations approximately ten-fold higher than the minimum effective dose for the transforming ras oncoprotein. Thus, 15 ng of either normal ras protein or ras$^{lys12ser186}$, a protein that cannot associate with the plasma membrane (B. M. Willumsen et al., *EMBO J.*, 3, 2581 (1984); R. Kim et al., *Mol. Cell. Biol.*, 10, 5945 (1990)), had no effect on the division of embryonic cells. Likewise, the injection of a dominant negative mutant, with a preferential affinity for GDP, ras$^{lys12asn17}$ (L. A. Feig et al., *Mol. Cell. Biol.*, 8, 3235 (1988)) was ineffective at ceasing cell division, as was ras$^{lysΔ153-164}$, which is defective in GTP-binding (J. C. Lacal et al., *EMBO J.*, 5, 679 (1986)). To eliminate the possibility that arrest of embryonic cell division was due to some toxic effect of the ras oncoprotein, we coinjected two-to four-fold excess of the dominant negative mutant, ras$^{lys12asn17}$ p21, along with the ras$^{lys12}$ oncoprotein. In these experiments, the ras-induced cleavage arrest was markedly suppressed. Thus, only the ras product displaying oncogenic activity can cause embryonic cleavage arrest.

To ascertain whether embryonic cell division was arrested at metaphase, extracts prepared from ras oncogene-arrested embryos were assayed biologically and biochemically for MPF activity. Extracts from both mos and ras-arrested embryos exhibited high levels of MPF, as assayed in cycloheximide-treated oocytes. Moreover, extracts from embryos arrested by either the ras oncogene or authentic CSF had equally high levels of MPF-associated histone H1 kinase activity when compared to the amount detected in extracts from control-activated eggs. Thus, the ras oncoprotein can arrest cleaving embryos in mitosis, as evidenced by the presence of high levels of MPF and the associated histone H1 kinase activity. The above results demonstrate a new biological activity as well as a new assay for the ras oncoprotein, but raise the question of whether m is required for the CSF-like activity. Even though the mos product is not always required for ras oncogene-induced meiotic maturation (Table 1), it is routinely synthesized (data not shown). Since endogenous mos RNA is present through the late blastula stage (N. Sagata et al., *Nature*, 335, 519 (1988)) and could be translated during mitosis, we examined embryos arrested in cleavage by the ras oncogene for pp39$^{mos}$ expression. H-ras$^{val12}$ RNA transcripts were coinjected with $^{35}$S-labeled cysteine into both blastomeres of 2-cell embryos and compared to blastomeres injected with 0.3 ng of mos RNA, an amount too low to display CSF activity (N. Sagata et al., *Nature*, 342, 512 (1989)). After 3 hours, when cleavage arrest was visible in ras-injected blastomeres, extracts were subjected to immunoprecipitation analyses with a Xenopus mos-specific monoclonal antibody (N. Sagata et al., *Science*, 245, 643 (1989)). These analyses show that radiolabeled pp39$^{mos}$ was detected only in the mos RNA-injected embryos, not in embryos arrested by the ras oncogene product, and argue that the mos product does not participate in the ras-induced arrest. Our studies identify an important new activity for the ras oncoprotein that links its function to the M-phase of the cell cycle. Moreover, cleavage arrest is a rapid assay for ras oncogenic potential. The rise in MPF activity at the end of interphase is responsible for entry into mitosis, while its decline allows entry into the next interphase (A. W. Murray et al., *Science*, 246, 614 (1989)). The ras oncoprotein can induce meiosis or arrest embryonic cells in mitosis and therefore must directly or indirectly influence M-phase events. Although it is known that insulin-induced meiotic maturation occurs through a pathway requiring endogenous p21$^{ras}$ as well as mos function (N. Sagata et al., *Nature*, 335, 519 (1988); A. K. Desphande et al., *Mol. Cell. Biol.*, 7, 1285 (1987); L. J. Korn et al., *Science*, 236, 840 (1987)), oncogenic ras, in fully grown stage VI oocytes, can induce maturation through a mos-independent pathway (Table 1). The high levels of MPF observed in the mature oocytes or in the ras oncoprotein-arrested blastomeres are consistent with an arrest in metaphase.

CSF activity induced by the mos or ras oncogenes raises the question of how embryonic cleavage arrest relates to transformation of somatic cells. Cells acutely infected with Moloney murine sarcoma virus express high levels of mos product (J. Papkoff et al., *Cell*, 29, 417 (1982)), subsequently round up, and detach from the monolayer (P. J. Fischinger et al., *J. Gen. Virol.*, 13, 203, (1971)). This morphological alteration is reminiscent of the mitotic phenotype and could be an effect of CSF/mos activity (N. Sagata et al., *Nature*, 342, 512 (1989)). We have proposed that the selection for the mos-transformed phenotype is a selection for cells expressing levels of $pp39^{mos}$ that are ample for transformation but insufficient for CSF arrest (N. Sagata et al., *Nature*, 342, 512 (1989)). The ras oncoprotein has been reported to induce growth arrest at $G_2$ (T. Hirakawa et al., *Proc. Natl. Acad. Sci. U.S.A.*, 85, 1519 (1988)) or $G_2/M$ (A. J. Ridley et al., *EMBO J.*, 7, 1635 (1988)) when overexpressed in either REF52 (rat embryo fibroblast) or primary Schwann cells, respectively. Durkin and Whitfield (J. P. Durkin et al., *Mol. Cell. Biol.*, 7, 444 (1987)) have shown that in NRK cells, Ki-ras p21 promotes $G_2/M$ transition in serum-free medium. Interestingly, high levels of ras oncoprotein expression ncrease the rate of abnormal mitosis in NIH/3T3 cells (N. Hayag et al., *Oncogene*, 5, 1481 (1990)). our data show that the activated ras oncogene roduct can induce oocyte maturation by using either mos-dependent or -independent pathways. Masui and co-workers have described a secondary CSF activity (P. G. Meyerhof et al., *Devel. Biol.* 61, 214 (1977); E. Shibuya et al., *Development*, 106, 799 (1989)) that develops after primary CSF/mos is inactivated (N. Sagata et al., *Nature*, 342, 512 (1989); N. Watanabe et al., *Nature*, 342, 505 (1989)) indicating that parallel pathways exist. The ras oncogene product exhibits CSF-like activity in embryos without the assistance of $pp39^{mos}$ and provides additional evidence that other products possess CSF activity. CSF may mediate cell cycle arrest through a feedback mechanism that stabilizes high levels of MPF (A. W. Murray et al., *Science*, 246, 614 (1989)). Presently, we do not know whether oncogenic ras functions in M-phase by inducing MPF activity, or whether it stabilizes MPF activity by functioning through a feedback control mechanism that prevents MPF degradation.

EXAMPLE 3

The effect of varying the paclitaxel concentrations in the media of transformed and non-transformed fibroblasts.

FIG. 6 shows the growth curves of transformed (by Xenopus c-mos over-expression) and non-transformed 3T3 fibroblasts. These experiments were carried out by plating 50,000 cells per 35 mm dish. The media was changed at t=0 hrs to media containing 0, 0.25 and 0.5 micromolar paclitaxel. The top left figure shows the growth of the non-transformed fibroblasts at the three taxol concentrations, which inhibit, but do not arrest growth. The top right figure shows the growth of the transformed fibroblasts at the three paclitaxel concentrations. As can be seen, the paclitaxel completely arrests the growth of the cells. The bottom three graph compare the growth of non-transformed versus transformed cells at each of the three paclitaxel concentrations. As can be seen, the growth characteristics of the transformed and non-transformed cells in the absence of paclitaxel is quite similar.

EXAMPLE 4

The inhibition of "focus formation" of mos-transformed fibroblasts by paclitaxel was accomplished as follows:

Mouse fibroblasts (3T3) transformed by over-expression of the Xenopus-mos proto-oncogene were mixed with non-transformed 3T3 fibroblasts at three dilutions to form three mixtures having initial ratios of the number of non-morphologically transformed cells to morphologically transformed cells of 100:1, 1000:1 and 10,000:1. The cells were plated at a concentration of 500,000 cells per 60 mm dish. The cells were allowed to grow for 24 hours before changing the media. The media was changed every third day, with the plates being scored for focus formation on day 10. The plates were incubated either with medium containing 1 micromolar paclitaxel, or no paclitaxel. As can be seen from FIG. 7, paclitaxel completely inhibited the formation of transformant colonies at all three dilutions of cells.

EXAMPLE 5

The suitability of the SRB growth curve assay for drug synergy screening and the synergistic effect of cis-platinum concentrations in combination with taxol concentrations on Mu-met transformants and X-mos transformants are shown in FIGS. 8 and 9.

FIG. 8 shows the growth curves of Mu-met transformed cells. The top curve displays cell growth in the absence of cis-platinum and taxol. The middle curve indicates moderate growth inhibition in the presence of 2.5 $\mu$M cis-platinum. The bottom curve shows that the addition of 0.25 $\mu$M paclitaxel, a subtherapeutic concentration, essentially resulted in complete inhibition of the growth of Mu-met transformed cells.

Similarly, FIG. 9 shows the growth curves of X-mos transformed cells. The top curve displays cell growth in the absence of cis-platinum and taxol. The middle curve indicates moderate growth inhibition in the presence of 2.5 $\mu$M cis-platinum. The bottom curve shows that the addition of 0.25 $\mu$M paclitaxel, a subtherapeutic concentration, essentially resulted in complete inhibition of the growth of X-mos transformed cells.

As can be seen, cis-platinum and taxol at concentrations which alone would not completely inhibit the growth of the transformed cells have a synergistic effect in combination which completely inhibits the growth of the transformed cells.

EXAMPLE 6

The growth of 3T3 fibroblasts transformed by the murine and Xenopus c-mos, murine c-met and the human ras oncogene was accomplished as follows:

Non-transformed 3T3 mouse fibroblasts and 3T3 fibroblasts transformed by the murine and Xenopus c-mos, murine c-met and the human ras oncogene were subcutaneously injected into different groups of nude mice at a concentration of $10^6$ cells per ml. One milliliter of cell suspension was injected and the mice were evaluated at 10, 14, and 28 days for tumor formation. As can be seen in Table 6, all transformed cell lines were tumorigenic in nude mice and gave palpable tumors within seven to ten days after injection. No tumors were observed in mice injected with the parental 3T3 cells after four weeks.

TABLE 6

Tumor formation

| Cell line | Tumors at 10 days | Tumors at 2 weeks | Tumors at 4 weeks |
|---|---|---|---|
| 3T3 | 0 cm, 0 cm, 0 cm | 0 cm, 0 cm, 0 cm | 0 cm, 0 cm, 0 cm |
| X-mos | 2.0 cm, 1.8 cm, 1.9 cm | >4 cm, >4 cm, >4 cm | sacrificed |
| Mu-mos | 2.0 cm, 2.1 cm, 1.5 cm | >4 cm, >4 cm, >4 cm | sacrificed |
| Mu-ras | 2.0 cm, 1.5 cm, 1.0 cm | >4 cm, >4 cm, >4 cm | sacrificed |
| Mu-met | 0.3 cm, 0.6 cm, 0.5 cm | 2.7 cm, 2.0 cm, 1.6 cm | sacrificed |

EXAMPLE 7

The inhibition of "focus formation" of mos-transformed fibroblasts by paclitaxel, doxorubicin, cis-platinum and methotrexate was evaluated as follows:

Mouse fibroblasts (3T3) transformed by the Xenopus mos protooncogene were mixed with non-transformed 3T3 fibroblasts at three ratios of dilution: 100:1, 1000:1 and 10,000:1. The cell suspensions were plated at a concentration of 500,000 cells per 35 mm dish and were allowed to attach for 24 hours before changing the medium. One micromolar paclitaxel was utilized in the treated plates. The medium was changed every third day, and plates were scored for focus formation on day 10. The same procedure was repeated for doxorubicin, cis-platinum and methotrexate. The resulting data is set forth in FIGS. 10 and 11. As can be seen by comparing FIGS. 10 and 11, paclitaxel completely inhibited the formation of transformant colonies at all three dilutions of cells, while doxo rubicin, cB-platinum and methotrexate exhibited little to no inhibition of focus formation.

EXAMPLE 8

The inhibition of "focus formation" of ras-transformed fibroblasts by paclitaxel, doxorubicin, cis-platinum and methotrexate was evaluated by repeating the procedure in Example 7 with ras oncogene transformed fibroblasts. The resulting data is set forth in FIG. 12. As can be seen by comparing FIGS. 10 and 12, paclitaxel completely inhibited the formation of transformant colonies at all three dilutions of cells. Doxorubicin exhibited some inhibitory effect on focus formation. Cis-platinum and methotrexate showed only a slight effect on the transformant colonies as to the inhibition of focus formation.

EXAMPLE 9

The inhibition of "focus formation" of murine mos-transformed fibroblasts by paclitaxel, doxorubicin, cis-platinum and methotrexate was evaluated by repeating the procedure in Example 7 with murine mos oncogene transformed fibroblasts. The resulting data is set forth in FIG. 13. As can be seen from comparing FIGS. 10 and 13, paclitaxel and doxorubicin completely inhibited the formation of transformant colonies at all three dilutions of cells. Cis-platinum and methotrexate showed only a slight effect on the transformant colonies as to the inhibition of focus formation.

EXAMPLE 10

The inhibition of "focus formation" of murine c-met transformed fibroblasts by paclitaxel, doxorubicin, cis-platinum and methotrexate was evaluated by repeating the procedure of Example 7 with murine c-met oncogene transformed fibroblasts. The resulting data is set forth in FIG. 14. As can be seen by comparing FIGS. 10 and 14, paclitaxel has a significant effect on the transformant colonies at all three dilutions of cells. Doxorubicin, cis-platinum and methotrexate showed only a slight difference in effect on the transformant colonies as compared to the parental 3T3 cells as to the inhibition of focus formation.

All of the references cited herein are hereby incorporated in their entireties by reference.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

We claim:

1. A method of treating cancer by administering to a human paclitaxel and a DNA cross-linking anti-neoplastic agent, wherein said paclitaxel and DNA cross-linking anti-neoplastic agent act synergistically to inhibit cancerous cell growth in said human.

2. The method of claim 1, wherein said DNA cross-linking anti-neoplastic agent exerts an effect on a human cell division cycle during $G_1$ or S phase to inhibit cancerous growth.

3. The method of claim 2, wherein said DNA cross-linking anti-neoplastic agent exerts an effect on a human cell division cycle during S phase to inhibit cancerous growth.

4. The method of claim 1, wherein said DNA cross-linking anti-neoplastic agent is cisplatin.

5. The method of claim 4, wherein said DNA cross-linking anti-neoplastic agent exerts an effect on a human cell division cycle during $G_1$ or S phase to inhibit cancerous growth.

6. The method of claim 5, wherein said DNA cross-linking anti-neoplastic agent exerts an effect on a human cell division cycle during S phase to inhibit cancerous growth.

7. A method of treating cancer by administering to a human paclitaxel and a DNA cross-linking anti-neoplastic agent, wherein said paclitaxel exerts an effect on a human cell division cycle during M phase to inhibit cancerous growth, said DNA cross-linking anti-neoplastic agent exerts an effect on a human cell division cycle during $G_1$ or S phase to inhibit cancerous growth, and said paclitaxel and DNA cross-linking anti-neoplastic agent act synergistically to inhibit cancerous cell growth in said human.

8. The method of claim 7, wherein said DNA cross-linking anti-neoplastic agent exerts an effect on a human cell division cycle during S phase to inhibit cancerous growth.

9. The method of claim 7, wherein said DNA cross-linking anti-neoplastic agent is cisplatin.

10. The method of claim 9, wherein said DNA cross-linking anti-neoplastic agent exerts an effect on a human cell division cycle during S phase to inhibit cancerous growth.

11. A method of treating cancer by administering to a human paclitaxel and a DNA cross-linking anti-neoplastic agent, wherein said paclitaxel and DNA cross-linking anti-neoplastic agent are administered within eight hours of each other and act synergistically to inhibit cancerous cell growth in said human.

12. The method of claim 11, wherein said DNA cross-linking anti-neoplastic agent exerts an effect on a human cell division cycle during $G_1$ or S phase to inhibit cancerous growth.

13. The method of claim 11, wherein said DNA cross-linking anti-neoplastic agent exerts an effect on a human cell division cycle during S phase to inhibit cancerous growth.

14. The method of claim 11, wherein said DNA cross-linking anti-neoplastic agent is cisplatin.

15. The method of claim 14, wherein said DNA cross-linking anti-neoplastic agent is administered so as to exert an effect on a human cell division cycle during $G_1$ or S phase to inhibit cancerous growth.

16. The method of claim 15, wherein said DNA cross-linking anti-neoplastic agent is administered so as to exert an effect on a human cell division cycle during S phase to inhibit cancerous growth.

17. A method of treating cancer by administering to a human paclitaxel and a DNA cross-linking anti-neoplastic agent, wherein said placlitaxel exerts an effect on a human cell division cycle during M phase to inhibit cancerous growth, said DNA cross-linking anti-neoplastic agent exerts an effect on a human cell division cycle during $G_1$ or S phase to inhibit cancerous growth, said paclitaxel and DNA cross-linking anti-neoplastic agent are administered within eight hours of each other, and said paclitaxel and DNA cross-linking anti-neoplastic agent act synergistically to inhibit cancerous cell growth in said human.

18. The method of claim 17, wherein said DNA cross-linking anti-neoplastic agent exerts an effect on a human cell division cycle during S phase to inhibit cancerous growth.

19. The method of claim 17, wherein said DNA cross-linking anti-neoplastic agent is cisplatin.

20. The method of claim 19, wherein said wherein said DNA cross-linking anti-neoplastic agent is administered so as to exert an effect on a human cell division cycle during S phase to inhibit cancerous growth.

21. A method of treating cancer by administering to a human paclitaxel and DNA cross-linking anti-neoplastic agent, wherein said paclitaxel and DNA cross-linking anti-neoplastic agent are administered within one hour of each other and act synergistically to inhibit cancerous cell growth in said human.

22. The method of claim 21, wherein said DNA cross-linking anti-neoplastic agent exerts an effect on a human cell division cycle during $G_1$ or S phase to inhibit cancerous growth.

23. The method of claim 22, wherein said DNA cross-linking anti-neoplastic agent exerts an effect on a human cell division cycle during S phase to inhibit cancerous growth.

24. The method of claim 17, wherein said DNA cross-linking anti-neoplastic agent is cisplatin.

25. The method of claim 21, wherein said DNA cross-linking anit-neoplastic agent is administered so as to exert an effect on a human cell division cycle during $G_1$ or S phase to inhibit cancerous growth.

26. The method of claim 25, wherein said DNA cross-linking anti-neoplastic agent is administered so as to exert an effect on a human cell division cycle during S phase to inhibit cancerous growth.

27. A method of treating cancer by administering to a human paclitaxel and a DNA cross-linking anti-neoplastic agent, wherein said placlitaxel exerts an effect on a human cell division cycle during M phase to inhibit cancerous growth, said DNA cross-linking anti-neoplastic agent exerts an effect on a human cell division cycle during $G_1$ or S phase to inhibit cancerous growth, said paclitaxel and DNA cross-linking anti-neoplastic agent are administered within one hour of each other, and said paclitaxel and DNA cross-linking anti-neoplastic agent act synergistically to inhibit cancerous cell growth in said human.

28. The method of claim 27, wherein said DNA cross-linking anti-neoplastic agent exerts an effect on a human cell division cycle during S phase to inhibit cancerous growth.

29. The method of claim 27, wherein said DNA cross-linking anti-neoplastic agent is cisplatin.

30. The method of claim 29, wherein said DNA cross-linking anti-neoplastic agent is administered so as to exert an effect on a human cell division cycle during S phase to inhibit cancerous growth.

31. A method of treating cancer by administering to a human paclitaxel and a DNA cross-linking anti-neoplastic agent, wherein said paclitaxel and DNA cross-linking anti-neoplastic agent are administered to said human in such temporal proximity to each other so as to simultaneously achieve levels of said paclitaxel and DNA cross-linking anti-neoplastic agent in said human sufficient to act synergistically to inhibit cancerous cell growth in said human.

32. The method of claim 31, wherein said DNA cross-linking anti-neoplastic agent exerts an effect on a human cell division cycle during $G_1$ or S phase to inhibit cancerous growth.

33. The method of claim 32, wherein said DNA cross-linking anti-neoplastic agent exerts an effect on a human cell division cycle during S phase to inhibit cancerous growth.

34. The method of claim 31, wherein said DNA cross-linking anti-neoplastic agent is cisplatin.

35. The method of claim 34, wherein said DNA cross-linking anti-neoplastic agent is administered so as to exert an effect on a human cell division cycle during $G_1$ or S phase to inhibit cancerous growth.

36. The method of claim 35, wherein said DNA cross-linking anti-neoplastic agent is administered so as to exert an effect on a human cell division cycle during S phase to inhibit cancerous growth.

37. A method of treating cancer by administering to a human paclitaxel and a DNA cross-linking anti-neoplastic agent in such temporal proximity to each other so as to simultaneously achieve levels of said paclitaxel and DNA cross-linking anti-neoplastic agent in said human sufficient to act synergistically to inhibit cancerous cell growth in said human, wherein said paclitaxel exerts an effect on a human cell division cycle during M phase to inhibit cancerous growth, and said DNA cross-linking anti-neoplastic agent exerts an effect on a human cell division cycle during $G_1$ or S phase to inhibit cancerous growth.

38. The method of claim 37, wherein said DNA cross-linking anti-neoplastic agent exerts an effect on a human cell division cycle during S phase to inhibit cancerous growth.

39. The method of claim 37, wherein said DNA cross-linking anti-neoplastic agent is cisplatin.

40. The method of claim 39, wherein said DNA cross-linking anti-neoplastic agent is administered so as to exert an effect on a human cell division cycle during S phase to inhibit cancerous growth.

* * * * *